(12) United States Patent
Barlow et al.

(10) Patent No.: US 9,351,667 B2
(45) Date of Patent: May 31, 2016

(54) DEVICE, SYSTEM, AND METHOD FOR DETERMINATION OF ORAL/LIP STIFFNESS

(75) Inventors: Steven Barlow, Lawrence, KS (US); Douglas S. Kieweg, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 326 days.

(21) Appl. No.: 13/392,064

(22) PCT Filed: Aug. 26, 2010

(86) PCT No.: PCT/US2010/046787
§ 371 (c)(1),
(2), (4) Date: Mar. 22, 2012

(87) PCT Pub. No.: WO2011/028598
PCT Pub. Date: Mar. 10, 2011

(65) Prior Publication Data
US 2012/0271201 A1    Oct. 25, 2012

Related U.S. Application Data

(60) Provisional application No. 61/237,200, filed on Aug. 26, 2009.

(51) Int. Cl.
| | |
|---|---|
| A61B 5/117 | (2006.01) |
| A61B 5/103 | (2006.01) |
| A61B 5/11 | (2006.01) |
| A61B 5/22 | (2006.01) |
| A61B 5/0488 | (2006.01) |
| A61B 5/00 | (2006.01) |

(52) U.S. Cl.
CPC . *A61B 5/11* (2013.01); *A61B 5/228* (2013.01); *A61B 5/4082* (2013.01); *A61B 5/4088* (2013.01); *A61B 5/682* (2013.01); *A61B 5/0488* (2013.01); *A61B 5/4519* (2013.01); *A61B 5/6819* (2013.01)

(58) Field of Classification Search
None
See application file for complete search history.

(56) References Cited

U.S. PATENT DOCUMENTS

| | | | | |
|---|---|---|---|---|
| 4,432,376 | A | * | 2/1984 | Huszar .......................... 600/587 |
| 5,178,132 | A | * | 1/1993 | Mahefky ....................... 600/194 |
| 5,381,799 | A | | 1/1995 | Hamilton et al. |
| 5,772,605 | A | * | 6/1998 | Weijand ........................ 600/547 |

(Continued)

OTHER PUBLICATIONS

International Search Report dated Apr. 26, 2011 as received in application No. PCT/US2010/046787.
Written Opinion of the International Searching Authority dated Apr. 26, 2011 as received in application No. PCT/US2010/046787.
Seibel Lana M., et al. "Automatic measurement of nonparticipatory stiffness in the perioral complex", Journal of Speech, Language and Hearing Research, American Speech-Language-Hearing Association, Rockville, MD, US. vol. 50, No. 5, Oct. 1, 2007, pp. 1272-1279.
Takafumi Susami, et al., "Quantitative Evaluation of the Shape and the Elasticity of Repaired Cleft Lip", The Cleft Palate-Craniofacial Journal, vol. 30, No. 3, May 1, 1993, pp. 309-312.
European Search Report dated Apr. 2, 2015 received in European Application No. 10814295.1.

*Primary Examiner* — Brian Szmal
*Assistant Examiner* — Matthew Kremer
(74) *Attorney, Agent, or Firm* — Maschoff Brennan, PLLC

(57) ABSTRACT

A device for measuring orofacial stiffness in a subject can include: two lip saddle attachment components configured for attachment to the lip saddles of a patients mouth; two elongate members, each being coupled with one of the lip saddle attachment components; a pivot member that couples the two elongate members at a pivot point opposite from the two lip saddle attachment components; an electronic sensor configured to sense the stiffness of the lips by sensing movement of the elongate members with respect to the pivot point, where the electronic sensor is operably coupled to each of the elongate members; and a pressure component configured move with respect to the pivot point so as to provide pressure to and/or receive pressure from the lip saddle attachment components.

21 Claims, 17 Drawing Sheets

(56) References Cited

U.S. PATENT DOCUMENTS

| | | | |
|---|---|---|---|
| 5,777,467 A * | 7/1998 | Arms et al. | 324/207.18 |
| 6,032,065 A * | 2/2000 | Brown | 600/383 |
| 6,050,961 A | 4/2000 | Arnold | |
| 2003/0039942 A1 * | 2/2003 | Phillips | 433/140 |
| 2003/0163065 A1 | 8/2003 | Nakao | |
| 2005/0065422 A1 * | 3/2005 | Kandori et al. | 600/407 |
| 2008/0183107 A1 | 7/2008 | Miller et al. | |

\* cited by examiner

DEVICE, SYSTEM, AND METHOD FOR DETERMINATION OF ORAL/LIP STIFFNESS

CROSS-REFERENCE TO RELATED APPLICATIONS

This patent application claims the benefit of U.S. provisional application 61/237,200, filed Aug. 26, 2009, which provisional application is incorporated herein by specific reference in its entirety.

This invention was made with government support under DC003311, DC005803, and DE013814 awarded by the National Institutes of Health. The government has certain rights in the invention.

BACKGROUND OF THE INVENTION

Limb and orofacial stiffness is modulated by central descending neural inputs to lower motor neurons, reflex gain, muscle and connective tissue properties, postural orientation to gravitational loads, and geometry of muscle attachments. A common approach for quantifying muscle stiffness involves imposing a specific displacement ($\Delta X$) on a muscle-tissue system (i.e., whole body, limb, jaw) and measuring the resultant force ($\Delta F$). The ratio of the resultant force to displacement yields a stiffness quotient ($\Delta F/\Delta X$). Muscle rigidity, regarded as the clinical correlate of stiffness, is used as a diagnostic method to evaluate neurologic status, document the effects of disease progression, pharmacological efficacy, and neurosurgical intervention.

Although biomechanical studies of limb rigidity have provided valuable insight into the neural regulation of limb movement disorders, similar application to orofacial systems has been tenuous primarily due to inadequate methods of transduction for the 'floating' perioral tissue complex. Limb muscles typically have tendonous attachments to bone, and utilize a combination of muscle spindle receptors and Golgi tendon organs to regulate stiffness about joints for postural and voluntary movements. The anatomical organization is much different for the lower face. Most perioral muscles have insertions into the integument of skin, interdigitate with neighboring muscle groups, and lack classic muscle spindle-tendon organs. Significant differences in mechanoreceptor representation are apparent between hand and orofacial systems. The neural mechanisms underlying stiffness regulation for the face and limb are likely to differ in their expression in health and disease.

Therefore, there is a need for improved devices and systems for measuring orofacial stiffness. It would be beneficial to be capable of obtaining real-time perioral stiffness measurements in unrestrained participants in health and disease. It would be advantageous to be able to perform passive 'non-participatory' perioral stiffness to provide clinicians a new techniques for evaluating efficacy of pharmacological and surgical intervention in the perioral system of patients with neuromotor disease, craniofacial anomalies (i.e., cleft lip), or traumatic injury (i.e., bomb blast, missile wounds, vehicular).

BRIEF SUMMARY OF THE INVENTION

In one embodiment, a device for measuring orofacial stiffness in a subject can include: two lip saddle attachment components configured for attachment to the lip saddles of a patients mouth; two elongate members, each being coupled with one of the lip saddle attachment components; a pivot member that couples the two elongate members at a pivot point opposite from the two lip saddle attachment components; an electronic sensor configured to sense the stiffness of the lips by sensing movement of the elongate members with respect to the pivot point, where the electronic sensor is operably coupled to each of the elongate members; and a pressure component configured move with respect to the pivot point so as to provide pressure to and/or receive pressure from the lip saddle attachment components.

In one embodiment, the orofacial stiffness device can include an electrode system for measuring the orbicularis oris superior (OOS) and orbicularis oris inferior (OOI). The electrode system being configured for determining whether the patient is actively moving, holding or tensing their lips. The electrode system can include: an electrode pair for monitoring the OOS, an electrode pair for monitoring the OOI, and a reference electrode.

In one embodiment, the orofacial stiffness device can include or be associated/used with a bite block.

In one embodiment, the orofacial stiffness device can include or be associated/used with an anchor configured for anchoring the device to the subject. The anchor can be configured as a chin anchor or nose anchor.

In one embodiment, the orofacial stiffness device can include or be associated/used with a computing system capable of being in communication with the sensor and pressure component, and with an electrode system.

In one embodiment, the orofacial stiffness device can be characterized by at least one of the following: the two lip saddle attachment components each include a feature configured for attachment to the lip saddles of the patient's mouth; the two elongate members form an even arm cantilever in a "X" shape or a "V" shape; the pivot point forms an intersection of the two elongate members; the electronic sensor is a differential variable reluctance transducer; and the pressure means is a pressure actuator.

In one embodiment, one or more of the two lip saddle attachments components can have an adjustment mechanism configured for widening or shortening distance between the two lip saddles.

In one embodiment, one or more of the electronic sensor or pressure component can be coupled to the elongate members through movable couplings.

In one embodiment, the pressure component is a pressure actuator. Optionally, a pressure generating component can be operably coupled to the pressure component.

In one embodiment, the sensor can be coupled to the pressure component and the pressure component is coupled to the elongate members. Otherwise, the sensor can be coupled to the elongate members through movable couplings.

In one embodiment, a system for measuring orofacial stiffness in a subject can include: an orofacial stiffness device as described herein; a bite block; an anchor coupled with the device, said anchor configured for anchoring the cantilever to the subject; an electrode system having an electrode pair for monitoring the orbicularis oris superior (OOS), an electrode pair for monitoring the orbicularis oris inferior (OOI), and a reference electrode; and a computing system in communication with the pressure actuator, differential variable reluctance transducer, and electrode system so as to be capable of receiving and/or transmitting data therebetween.

In one embodiment, an adhesive member can be included, which is configured for adhering the anchor to the subject. The anchor can be a chin anchor or a nose anchor.

In one embodiment, the system can be characterized by one or more of the following: the pressure component can be a pressure actuator that is fluidly coupled to a pressure generating device; the sensor can be mounted on the pressure component; the sensor can be in communication with a data conditioning device; the data conditioning device can be in communication with a data acquisition system; the electrode system can be in communication with an EMG amplifier; the EMG amplifier can be in communication with the data acquisition system; the pressure actuator can be in communication with a pressure sensor; the pressure generating device can be in communication with the pressure sensor; the pressure sensor can be in communication with a bridge amplifier; and the data acquisition system can be in communication with a computing system.

In one embodiment, the system can include a caliper measuring device.

In one embodiment, the present invention can include a method of measuring orofacial stiffness in a subject. Such a method can include: providing an orofacial stiffness device/system as described herein; attaching the OOS and OOI electrodes to the skin associated with the OOS and OOI, respectively; attaching the reference electrode to the skin in a location not associated with the OOS or OOI; measuring the mouth length between the lip saddles of the subject with the caliper measuring device; determining the resting distance between the lip saddles of the subject; adjusting the lip saddle attachment components to correspond with the resting distance between the lip saddles; attaching the lip saddle attachment components to the lip saddles of the subject; placing a bite bock in the subject's mouth; operating the data acquisition system to record data; increasing pressure in the pressure actuator to stretch the lip saddles apart; allowing the lip saddles to recoil; and recording and or manipulating data related to stretching and recoiling of the lip saddles with the computing system.

In one embodiment, the method can include one or more of the following: instructing patient to remain speechless and motionless, and relax lips without movement or pressure; manually pressurizing the pressure actuator so as to stretch the lip saddles; allowing the cantilever arms return to original resting position; measuring an interangle oral aperture at rest; estimating resting muscle length of lips; completing measurement of lip stiffness in 2 minutes or less; digitizing data from the pressure actuator and differential variable reluctance transducer; calculating stiffness coefficients in real time during elastic recoil of lip saddles; graphically displaying stiffness coefficient versus lip saddle span; determining stiffness for a specific lip saddle span; determining muscle activity pattern during non-passive stretch; or calibrating the device/system.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

Figure 5:
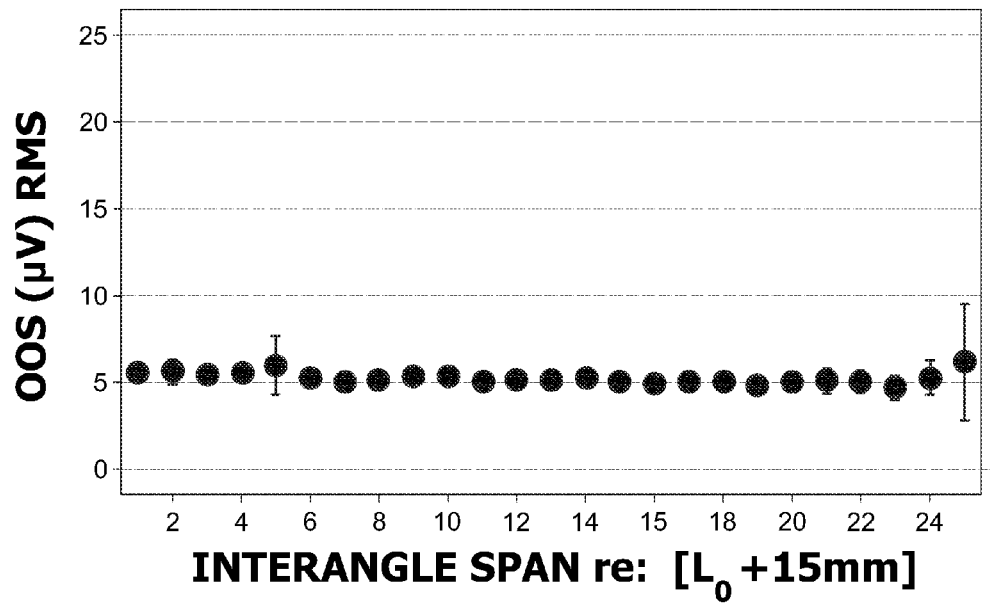
Figure 5:
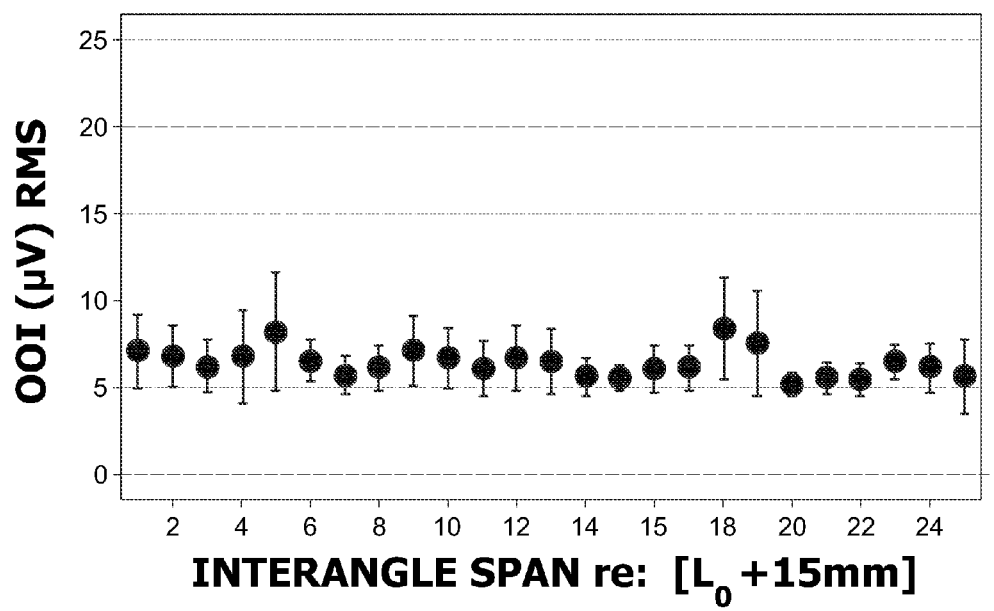

$$\hat{Y}_{ij}=0.04682-0.00442*\text{Span}_{ij}+0.00059\text{Span}_{ij}^2$$
Male regression equation $$\hat{Y}_{ij}=0.04583-0.00396*\text{Span}_{ij}+0.00054\text{Span}_{ij}^2$$
Female regression equation FIGS. 5A-5B include graphs that show the distribution of mean and standard error of EMG RMS values ($\mu$V) for upper lip (FIG. 5A) and lower lip (FIG. 5B) recording sites for all participants during the 'face-relaxed' non-participatory conditions.

Figure 6:
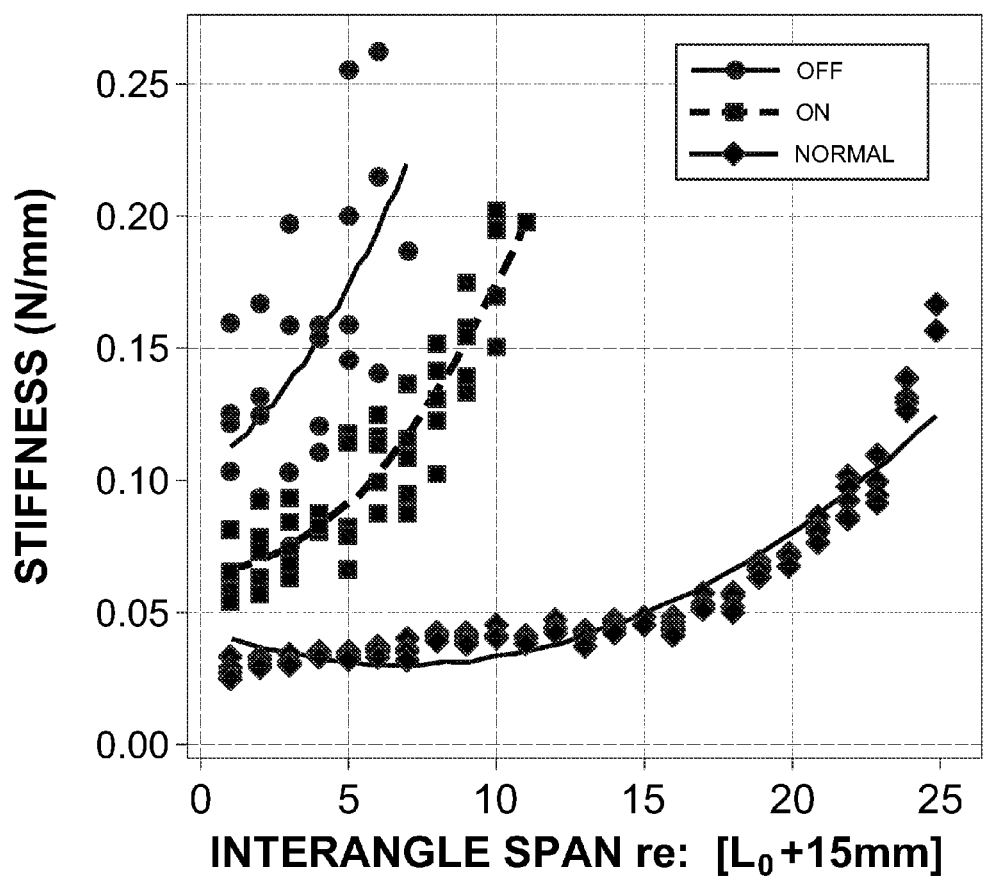

FIG. 6 includes a graph that illustrates perioral stiffness data and quadratic functions for a 68-year old male with Parkinson's disease in the ON (with anti-PD meds) and OFF (without meds) conditions plotted relative to an age- and sex-matched healthy control.

FIGS. 7A-7D illustrate embodiments of sub-miniature DVRT devices electronically coupled to a computing system.

DETAILED DESCRIPTION OF THE PREFERRED EMBODIMENTS

Generally, the present invention relates to a new device and automated measurement technology which is useful for measuring oral/facial stiffness, which device is referred to as an orofacial stiffness device. The orofacial stiffness device can be used to characterize non-participatory perioral stiffness in healthy adults for eventual application to patients with orofacial movement disorders associated with neuromotor disease, traumatic injury, or congenital clefts of the upper lip. Previous studies of perioral biomechanics required head stabilization for extended periods of time during measurement which precluded sampling patients with involuntary body/head movements (dyskinesias), or pediatric subjects. The orofacial stiffness device of the present invention is face-referenced, and does not require head-restraint, which is a significant advancement for patients.

The orofacial stiffness device can include a pneumatic glass air cylinder actuator configured for pressure changes, and an integrated subminiature displacement sensor for lip aperture changes. Perioral electromyograms can be simultaneously sampled to confirm passive muscle state for the superior and inferior divisions of the orbicularis oris muscles. Perioral stiffness, derived as a quotient from resultant force ($\Delta F$) and interangle span ($\Delta X$), can be modeled with multi-level regression techniques. Real-time calculation of the perioral stiffness function can provide a significant quadratic relation between imposed interangle stretch and resultant force. This stiffness growth function can differ significantly between males and females.

The orofacial stiffness device can be a cost-effective and non-invasive stimulus generation, and can allow for derivation of perioral stiffness. For example, the orofacial stiffness device can be used to study the dose-dependent effects of a drug (e.g., Levodopa) on perioral stiffness in an individual, such as a patient with advanced Parkinson's disease who exhibited marked dyskinesia and rigidity.

In one embodiment, the present invention can include devices, systems, and methods of using the orofacial stiffness device for determining the stiffness of the lips, mouth, and other oral aspects. The devices, systems and methods can be utilized without the need for a head restraint during the determination of oral/lip stiffness. The devices, systems, and methods can be used to assess the progression of neuromotor diseases/disorders, assess the effects of pharmacologic and/or surgical treatments of neurological disorders, and/or monitor or evaluate the effects of reconstructive surgery of the lower face (e.g., cleft lip). All of these functionalities of the present invention can be performed in real time, and data can be sampled at any point as needed or desired.

The present invention (e.g., devices, systems, and methods described herein) can be useful for alleviating the difficulties or problems associated with head restraint during the determination of oral/lip stiffness. Previously, a patient's head had to be secured to a cephalostat (e.g., headframe) to sample tissue biomechanics. Now with the present invention, such tissue biomechanics can be sampled and obtained without having the patient's head secured to a cephalostat. The present invention is configured as a head-referenced medical device suitable for children and adults without head restraint. For various reasons, head restraints are inoperable for many instances where measuring oral stiffness is needed. Thus, the present invention is a significant advancement over the art.

The present invention is a substantial improvement over the prior devices because the head does not need to be restrained, which is nearly impossible for infants, children, patients with Parkinson's and the like. Also, the device and system allows for digital sampling of the oral/lip stiffness, which can be completed within 2 minutes, and often within a single minute. Additionally, the device and system are computerized, and includes including special purpose data acquisition and digital signal processing software to display and analyze lip force and displacement data to derive stiffness.

The present invention can be used to assess the progression of a neurodegenerative disorders or neuromotor disease (i.e., Parkinson's disease), assess the effects of pharmacologic or surgical treatment for neurological disorders (i.e., Parkinson's disease [PD], deep brain stimulation), or document the effects of reconstructive surgery of the lower face (i.e., cleft lip).

The term "neurodegenerative disorder" refers to a disorder in which progressive loss of neurons occurs either in the peripheral nervous system or in the central nervous system. Accordingly, the invention can be used to assess the progression of various neurodegenerative disorders, such as the following: chronic neurodegenerative diseases such as diabetic peripheral neuropathy, Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis ("ALS"), degenerative ataxias, cortical basal degeneration, ALS-Parkinson's-Dementia complex of Guam, subacute sclerosing panencephalitis, Huntington's disease, Parkinson's disease, multiple sclerosis, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Wernicke-Korsakoffs related dementia (alcohol induced dementia), Werdnig-Hoffmann disease, Kugelberg-Welander disease, Tay-Sach's disease, Sandhoff disease, familial spastic disease, Wohifart-Kugelberg-Welander disease, spastic paraparesis, progressive multifocal leukoencephalopathy, and prion diseases (including Creutzfeldt-Jakob, Gerstmann-Straussler-Scheinker disease, Kuru and fatal familial insomnia). Other conditions also included within the methods of the present invention include age-related dementia and other dementias, and conditions with memory loss including vascular dementia, diffuse white matter disease (Binswanger's disease), dementia of endocrine or metabolic origin, dementia of head trauma and diffuse brain damage, dementia pugilistica and frontal lobe dementia. Also other neurodegenerative disorders resulting from cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration). Thus, the term also encompasses acute neurodegenerative disorders such as those involving stroke, traumatic brain injury, schizophrenia, peripheral nerve damage, hypoglycemia, spinal cord injury, epilepsy, and anoxia and hypoxia.

In one embodiment, the neurodegenerative disorder can be selected from Alzheimer's disease, Parkinson's disease, amyotrophic lateral sclerosis, age-related memory loss, senility and age-related dementia. Preferably, the neurodegenerative disorder is Alzheimer's disease (an amyloidosis disorder). Other conditions within the methods of the present invention include other amyloidosis disorders which share features with Alzheimer's disease including, but not limited to, hereditary cerebral angiopathy, normeuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, and Finnish and Iowa amyloidosis.

Generally, the orofacial stiffness device can include: a means for hooking (e.g., hooking means) both of the corners (e.g., where the top lip intersects the bottom lip also known as the lip saddles) of a patient's mouth; an extended or elongate member that is coupled with each hooking means; a pivot point that couples the two elongate members opposite from the two hooking means; an electronic sensor means that senses the stiffness of the lips by sensing movement of the elongate members with respect to the pivot point, where the electronic sensor is operably coupled to each of the elongate members; and a pressure means that can cause the elongate members to move with respect to the pivot point so as to provide pressure to and/or receive pressure from the hooking means, and thereby the corners of the mouth. The hooking means can have various configurations and include features that can be attached to the lip saddles.

The orofacial stiffness device can also include or be associated with an electrode system for measuring the orbicularis oris superior (OOS) and orbicularis oris inferior (OOI) muscle activity, which can determine whether the patient is actively moving, holding or tensing their lips via electromyography (EMG).

The orofacial stiffness device can also include a bite bloc that can prevent the patient from biting down or otherwise moving the lower jaw.

The orofacial stiffness device can also include an anchor, such as a chin anchor or nose anchor that anchors the orofacial stiffness device to the patient's face. The anchor means allows for the device to move with the patient's head. The device/system can also include various computing systems for controlling aspects of the device or receiving data therefrom.

Figure 1A:
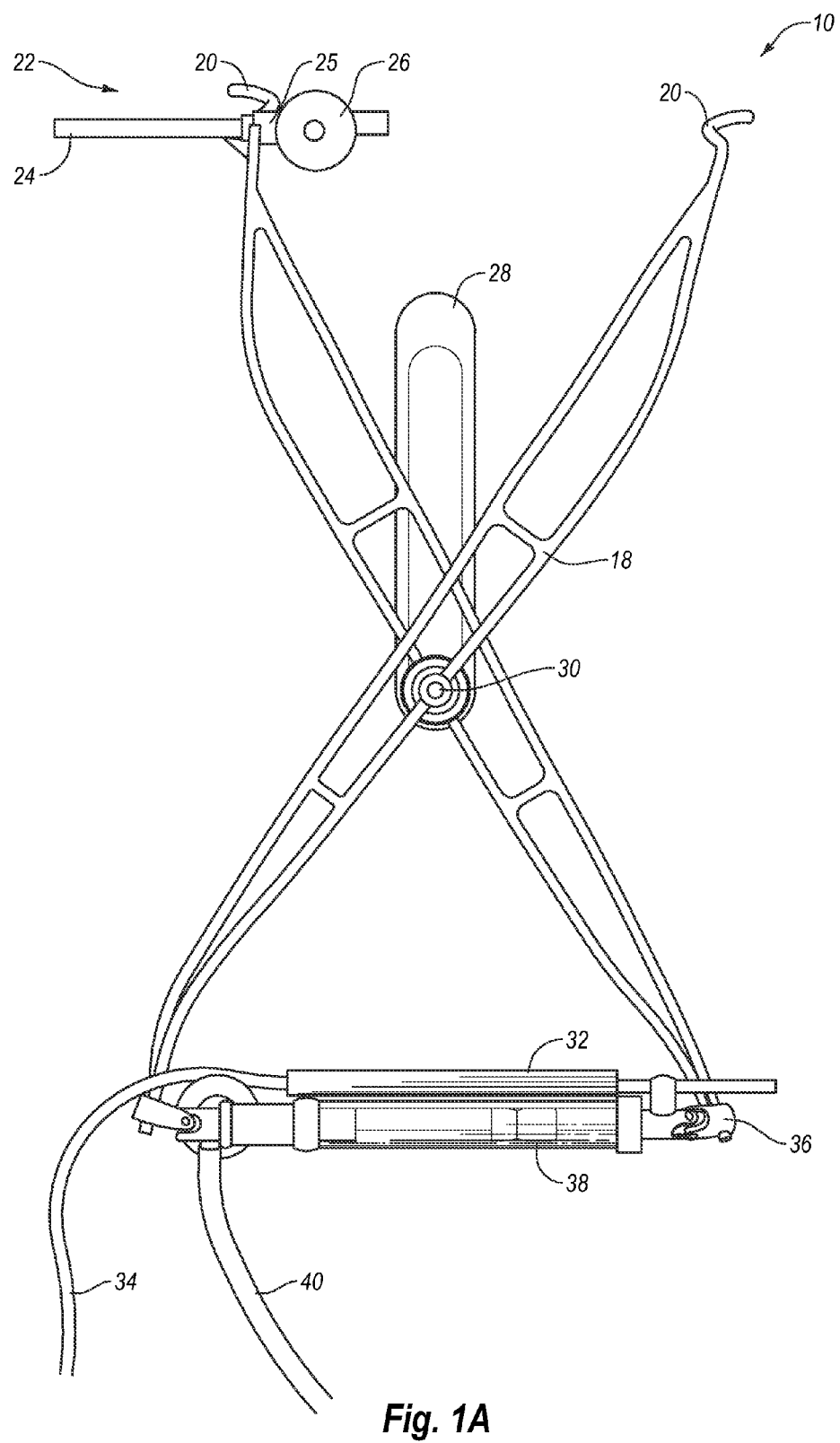
FIGS. 1A-1J include schematic representations of an embodiment of a device configuration to assess the force-displacement relation (stiffness) for the perioral tissues. The embodiments include equal-arm cantilevers (e.g., scissor) and lip saddles (e.g., hooks, which can be stainless steel or other medical grade material) positioned for measuring increases in interangle span and automated stiffness sampling. The embodiments include lip span adjustors configured to accommodate individual differences in lip aperture, and which can be used to set initial position ($L_0+15$ mm). The embodiment of FIG. 1A includes a chin anchor, which was positioned over the subject's mental symphysis for vertical stabilization as shown in FIG. 1B.
Figure 1B:
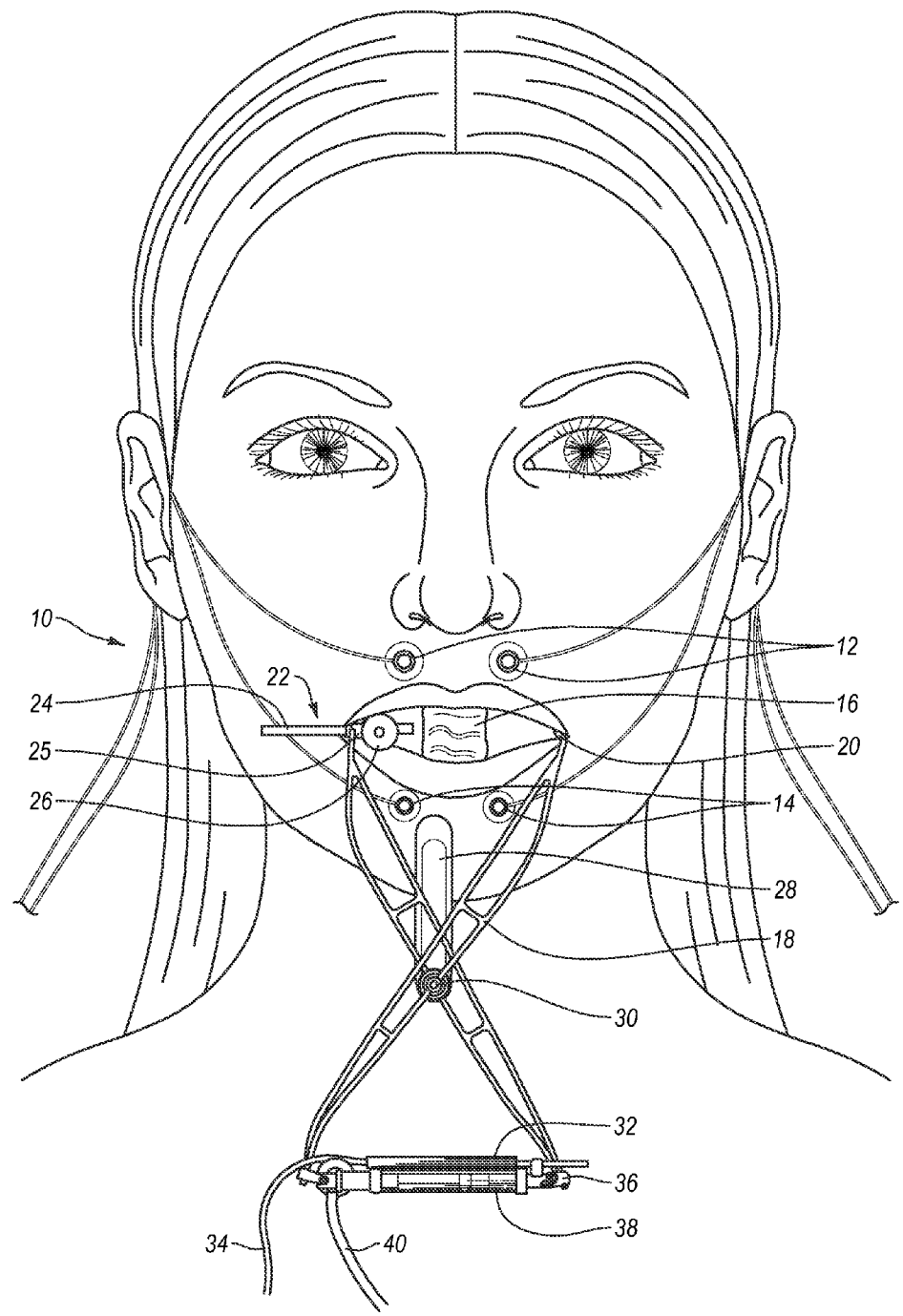

FIGS. 1A-1B include schematic representation of an embodiment of the orofacial stiffness device 10. The device 10 can include a pair of OOS electrodes 12 that measure the biocurrent generated by movement or stiffening of the OOS. The device 10 can include a pair of OOI electrodes 14 that measure the biocurrent generated by movement or stiffening of the OOI. Alternatively, the electrodes 12, 14 can be part of a kit or system. The device 10 can include a bite block 16, or the bite block 16 can be part of a kit or system. The device 10 can include a cantilevered structure 18 that has a lip hook 20 for each side of the lips opposite of a pivot point 30 that allows the lip hooks 20 to move with respect to each other. The structure 18 can include a lip interangle adjustor 22, which can further include a slidable member 24 coupled with at least one of the lip hooks and a receiver 25 for receiving the slidable member 24. An adjustment mechanism 26 can be used to tighten or loosen the slidable member 24 so that it can move with respect to the receiver 25.

As shown in FIG. 1B, the pivot point 30 can optionally be attached to an anchor 28, such as the chin anchor that is shown. The anchor 28 can be adhered to the face of the subject, such as to the chin as shown.

The device 10 is shown to be in an X shape with the pivot point 30 being at the intersection of the cantilever. At the other side of the "X" shape from the lip hooks 20, the device 10 can include a sensor 32 that is configured to sense whether or not the lip hooks 20 become closer or farther apart. The sensor 32 can be coupled to the structure 18 at movable couplings 36, such as ball couplings that allow for the cantilever to move with respect to the sensor 32. The sensor 32 can be connected to a data line 34 that can transmit data to a computing system (not shown).

Additionally, the same side of the device 10 can include a pressure member 38 that is also coupled to the structure 18 through movable couplings 36. The pressure member 38 can be a standalone member or it can receive pressure from an external source through a pressure line 40. The pressure member 38 is configured to use pressure to change the pressure at the lip hooks 20.

Alternatively, the sensor 32 can be physically coupled to the pressure member 38 and not directly to the structure 18. That is, the sensor 32 can be physically coupled to the pressure member 38, which pressure member is then physically coupled to the structure 18.

Figure 1C:
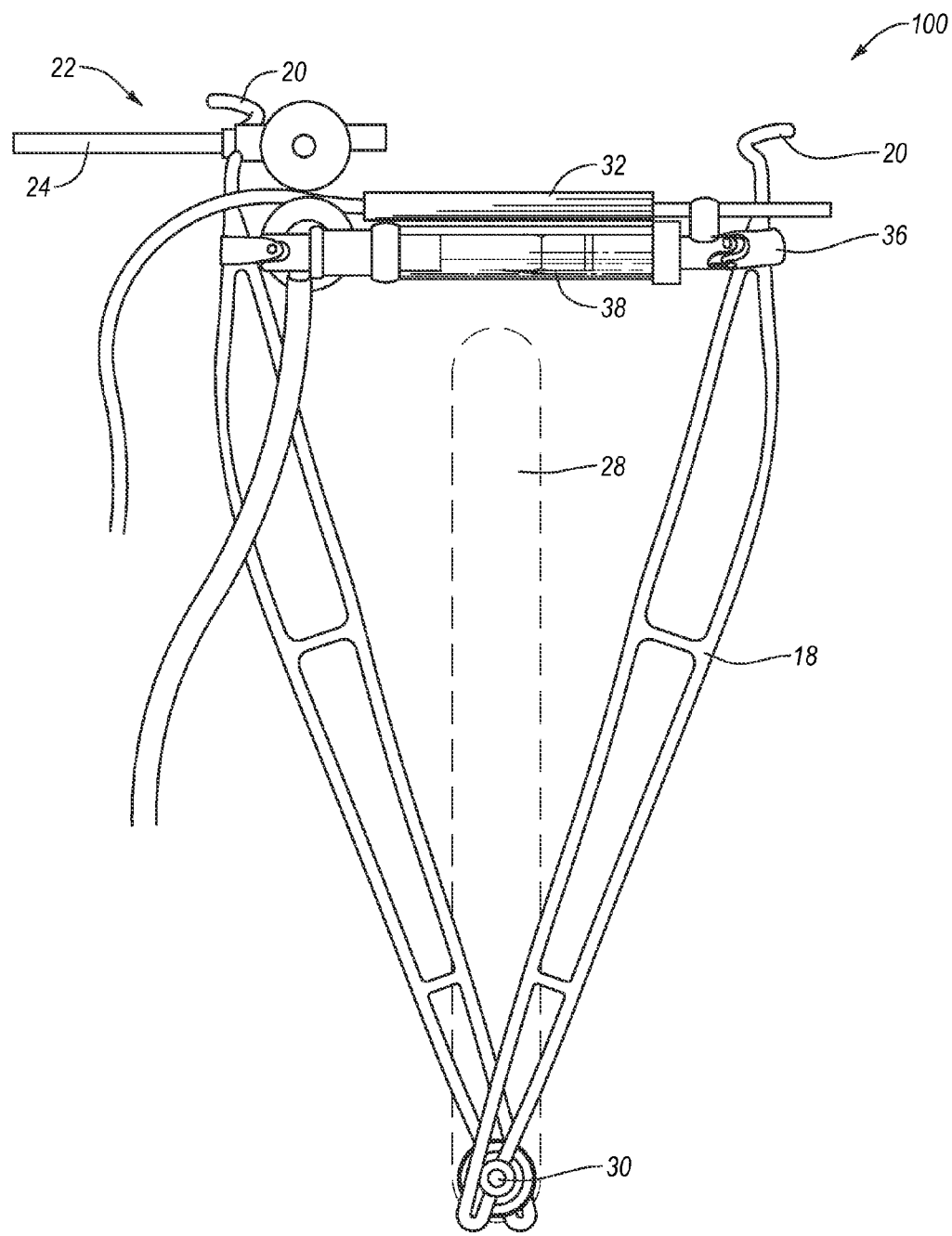
Figure 1D:
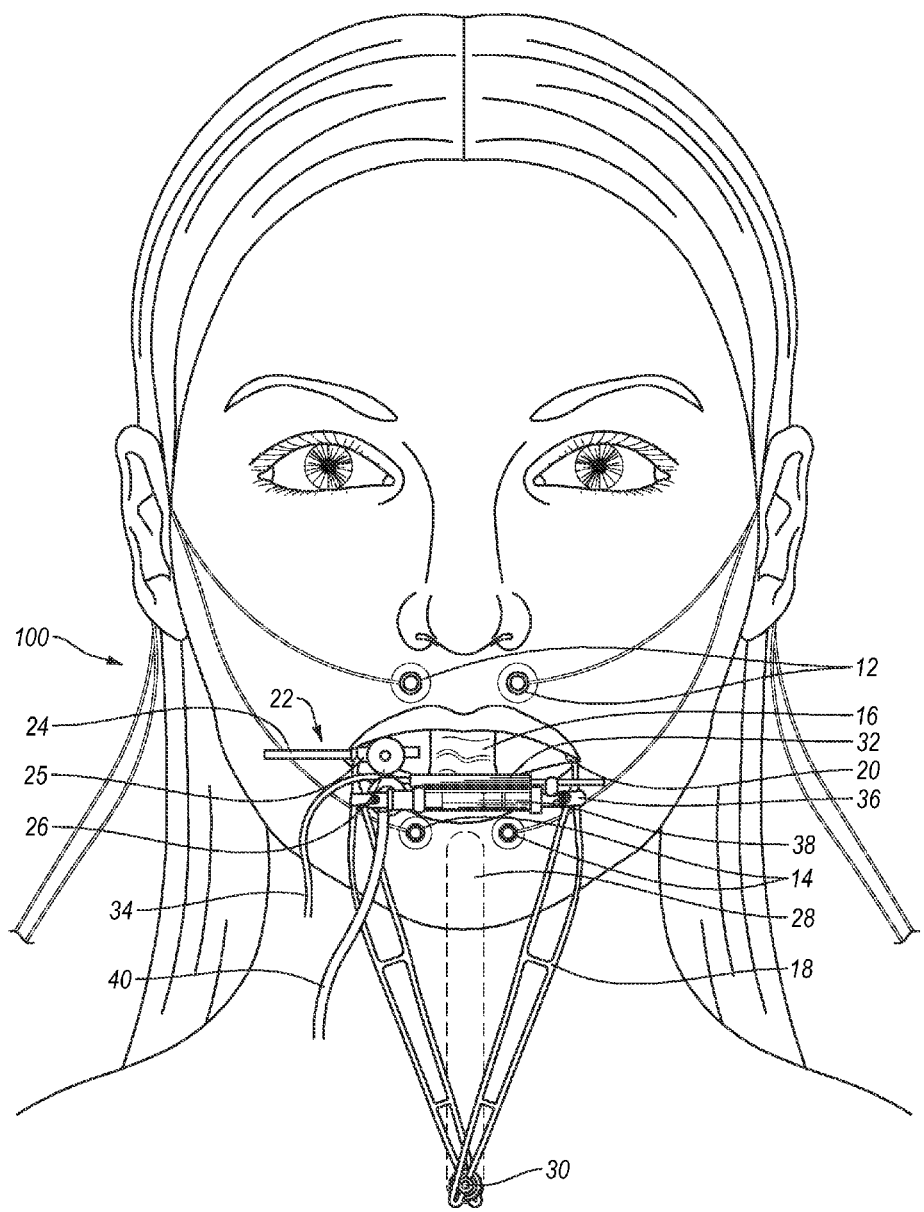

FIGS. 1C-1D include a schematic representation of another embodiment of an orofacial stiffness device 100. FIG. 1D shows the device 100 as attached to a subject's face. The orofacial stiffness device 100 can have many of the same components as the orofacial stiffness device 10 of FIG. 1A, even if not specifically shown. However, the configuration of the orofacial stiffness device 100 includes a "V" shape with the cantilever member 18 having a "V" shape with the pivot point 30 at the bottom. The cantilever member 18 can include the sensor 32 being coupled thereto above the pivot point 30 instead of below as shown in FIG. 1A. The sensor 32 can be coupled to the cantilever member 18 directly or indirectly through movable couplings 36. As shown, the sensor 32 is coupled to the pressure member 38, which in turn is coupled to the cantilever member 18 through movable couplings. The lip hooks 20 are also shown to be coupled to the cantilever member 18 through rotatable interangle adjusters. An optional anchor 28 (dashed lines) is shown to be configured for anchoring to the chin of a subject.

Figure 1E:
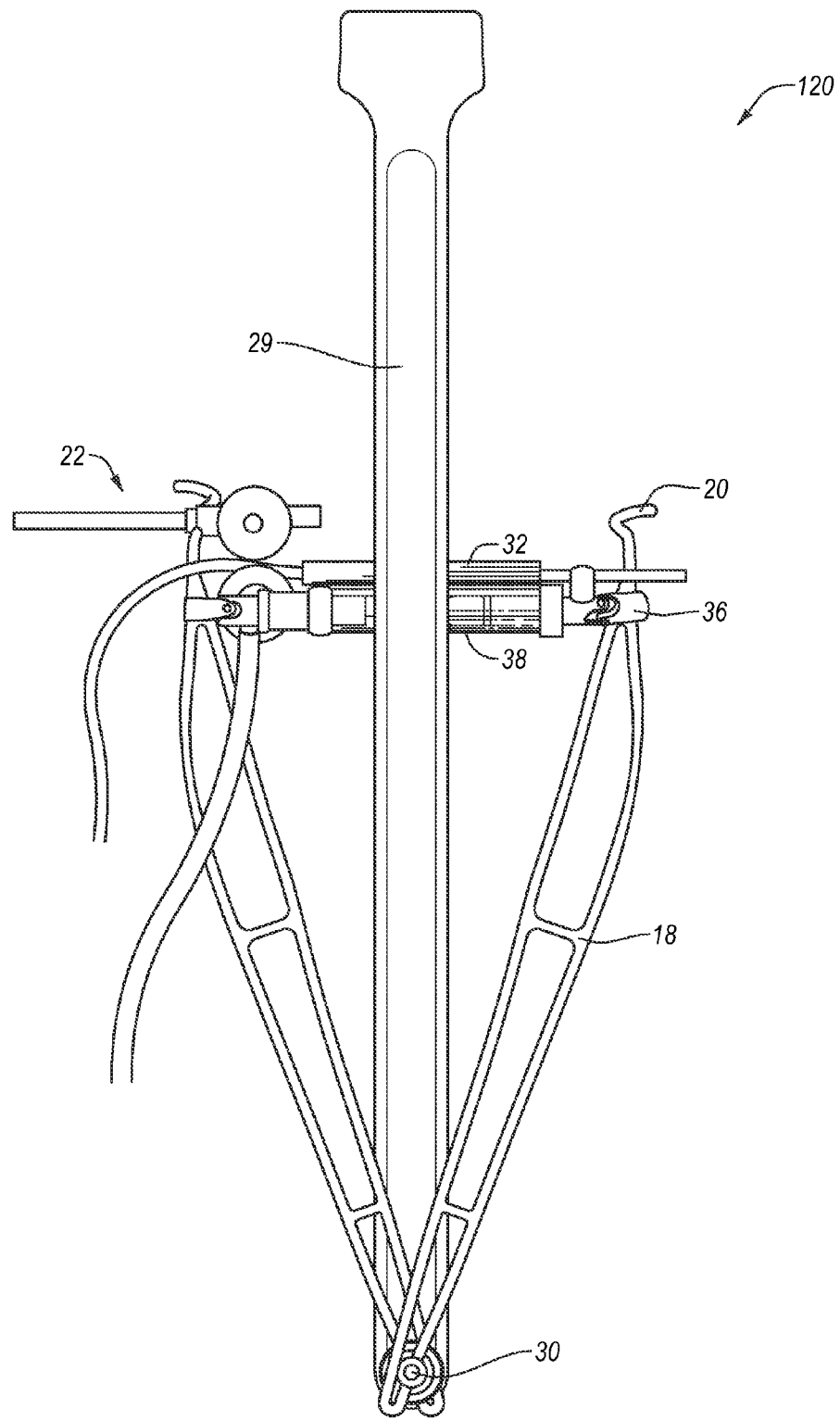
Figure 1F:
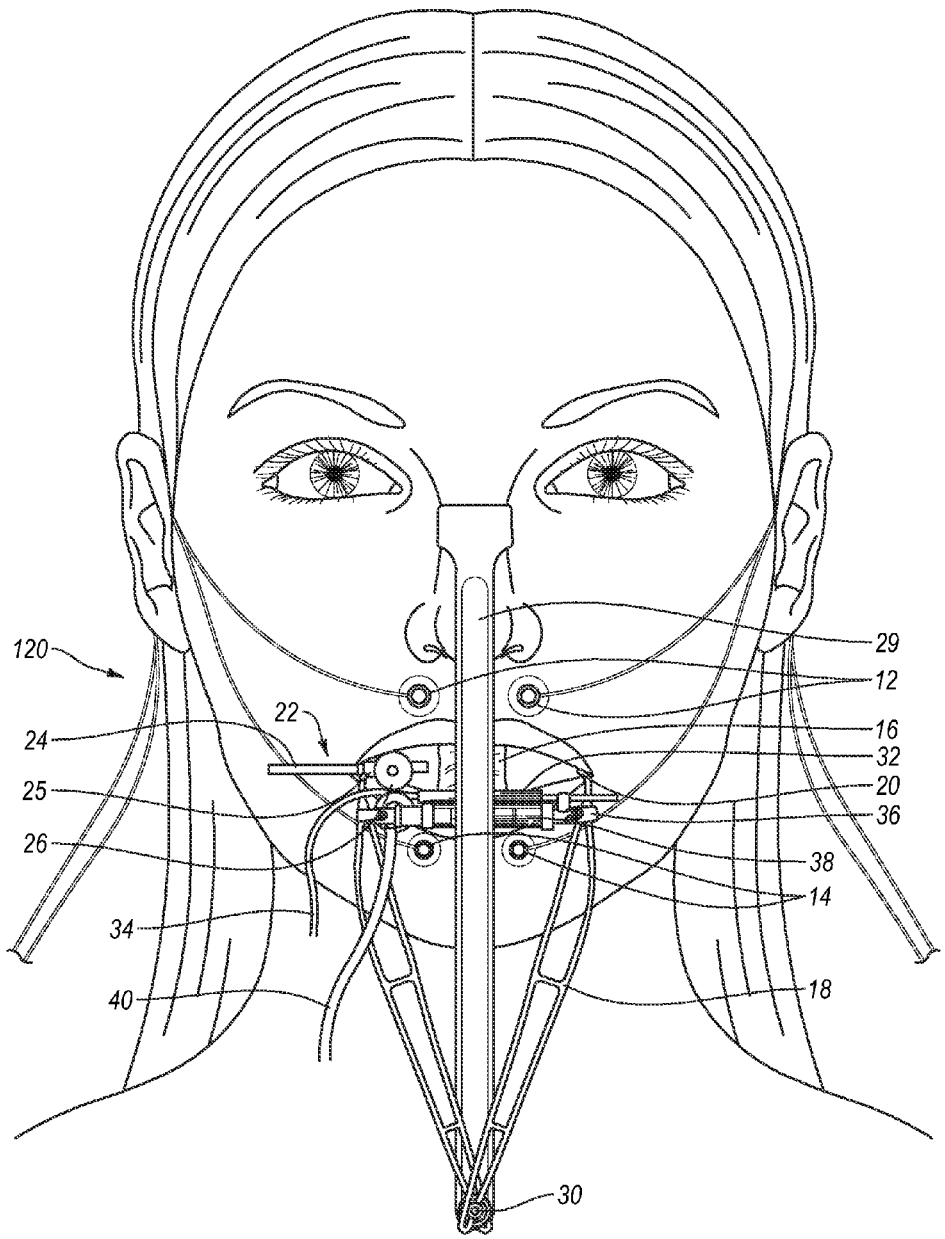

FIGS. 1E-1F include a schematic representation of another embodiment of an orofacial stiffness device 120 that is similar to the device 100 of FIG. 1C. The difference includes the device 120 having a nose anchor 29. FIG. 1F shows the device 120 as attached to a subject's face.

Figure 1G:
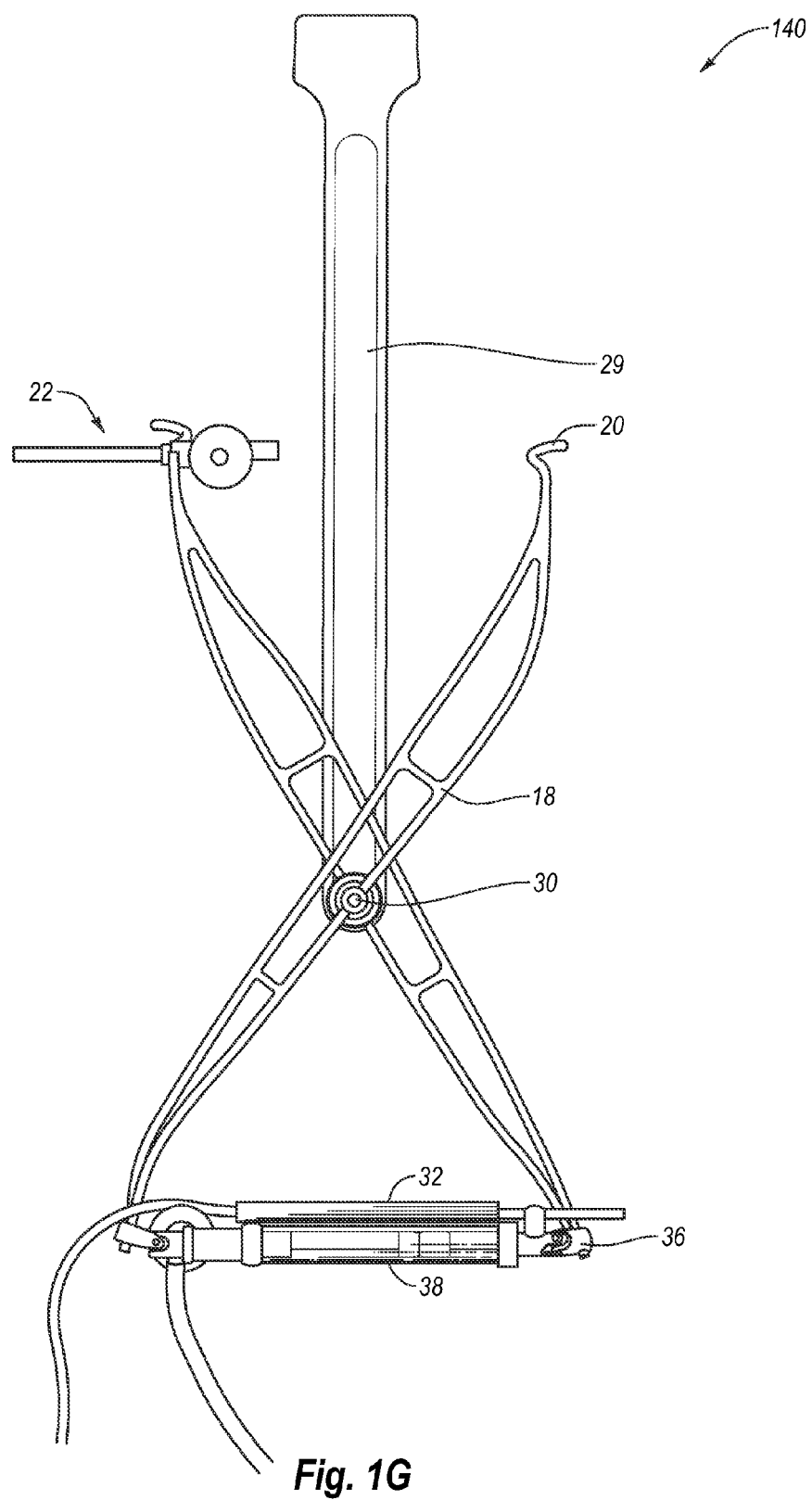
Figure 1H:
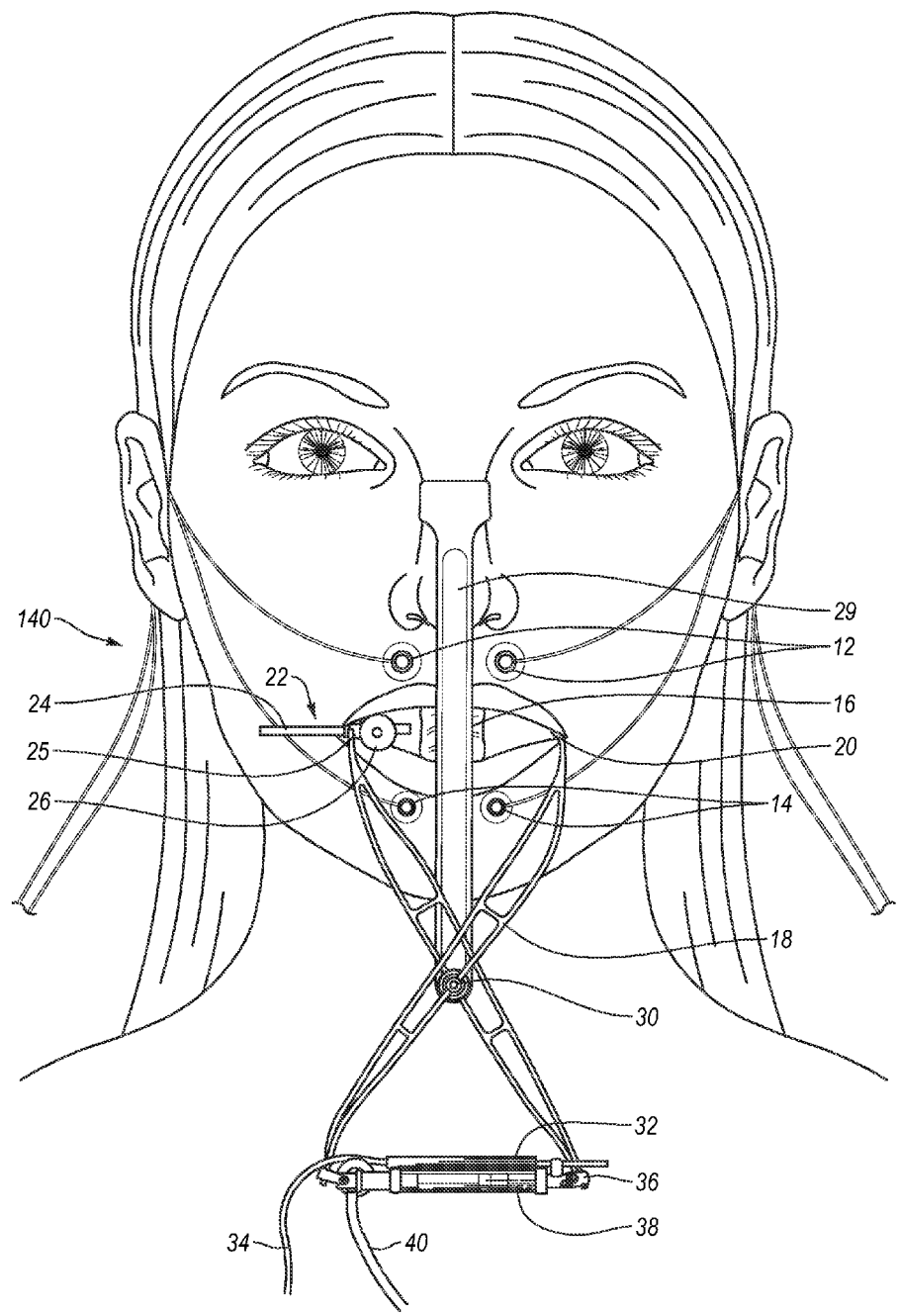

FIGS. 1G-1H include a schematic representation of another embodiment of an orofacial stiffness device 140 that is similar to the device 10 in FIG. 1A and the device 120 in FIG. 1E. Particularly, the device 120 is shaped like the device 10 of FIG. 1A, and includes a nose anchor 20. FIG. 1H shows the device 140 as attached to a subject's face.

Figure 1I:
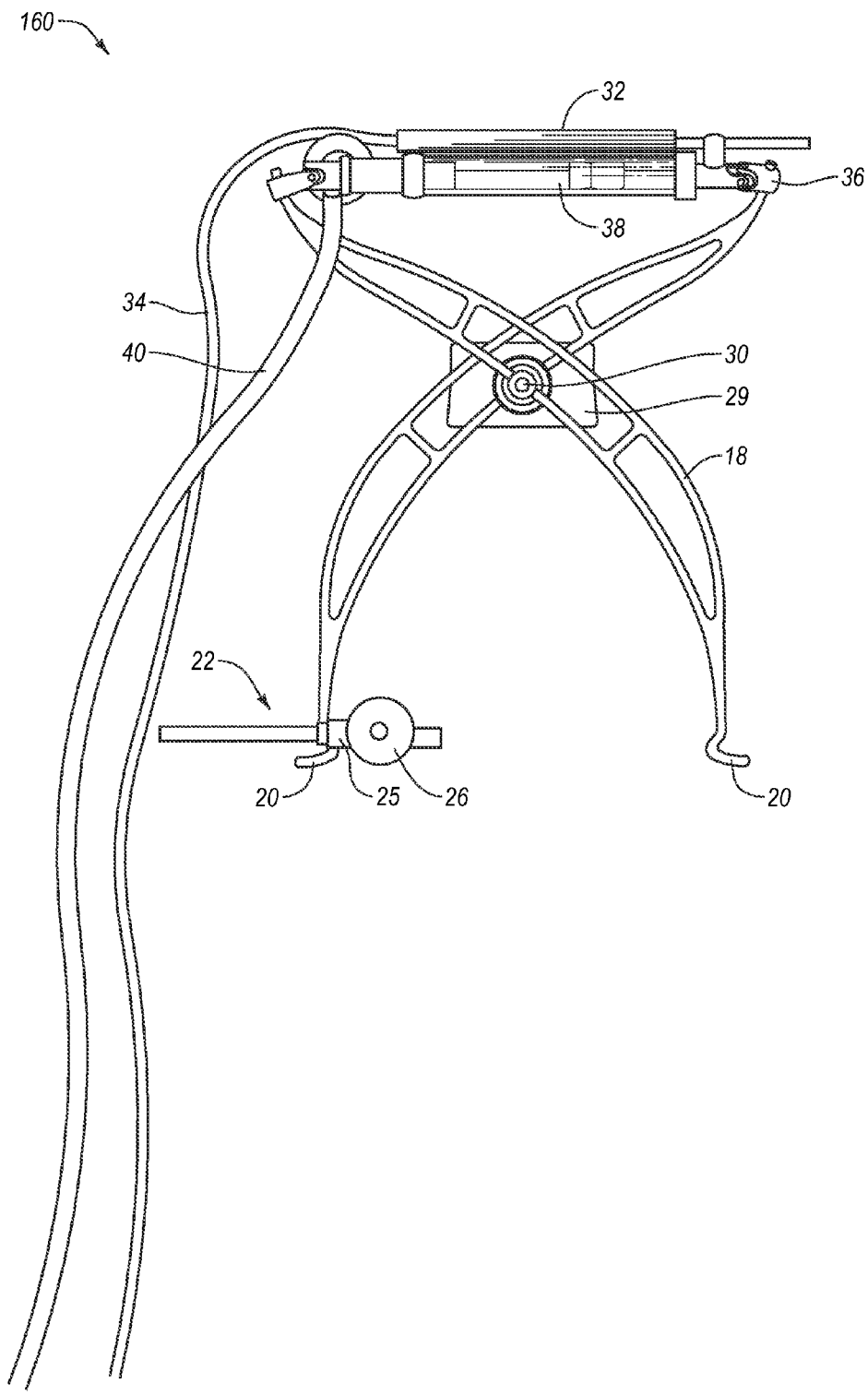
Figure 1J:
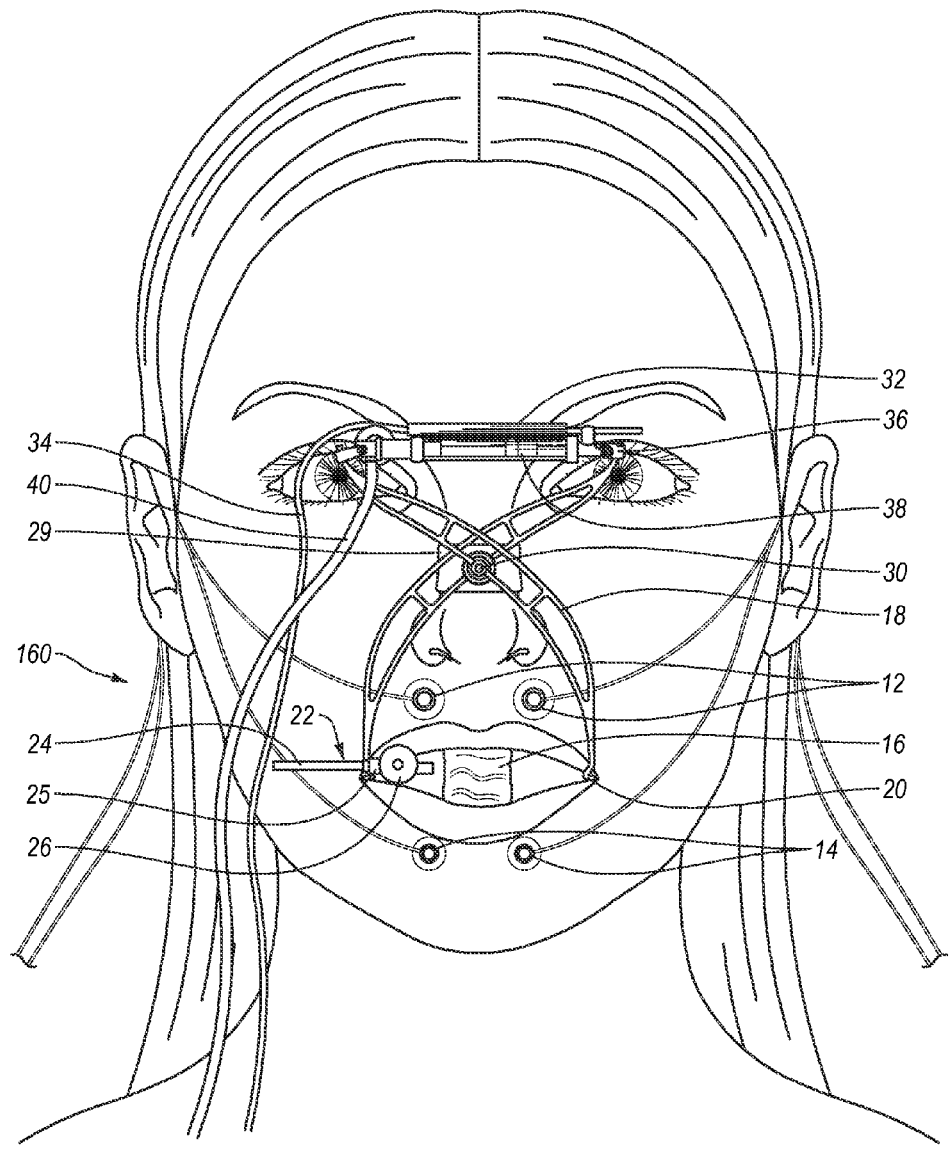

FIGS. 1I-1J include a schematic representation of another embodiment of an orofacial stiffness device 160. The device 160 includes features of the device 10 of FIG. 1A, however, the orientation is inverted. As such, the cantilever member 18 is positioned so that the lip hooks 20 are at a lower position compared to the sensor 32 and/or pressure member 38. Additionally, the cantilever member 18 is coupled to a nose brace 29 that supports the device 160 in the inverted orientation. FIG. 1J shows the device 160 as attached to a subject's face.

FIGS. 7A-7D illustrate embodiments of sub-miniature DVRT devices 732 electronically coupled to a computing system 706 through a cable 734. Also a DVRT connector 702 is shown to be capable of being connected to a computing system connector 704 with 4 leads. The DVRT connector 702 and computing system connector 704 are configured so that there is only one way in which they couple and connect.

Figure 7A:
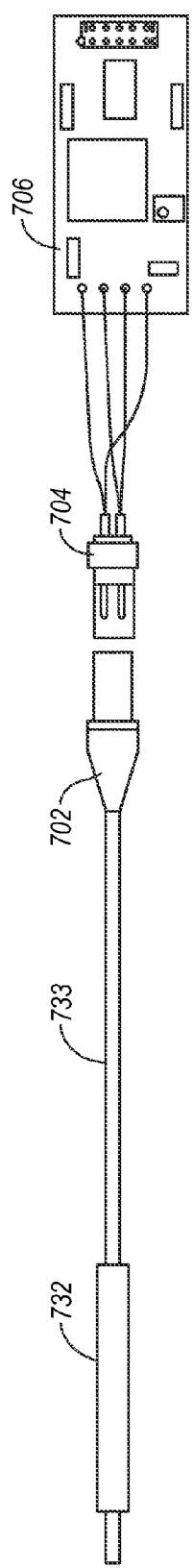
Figure 7B:
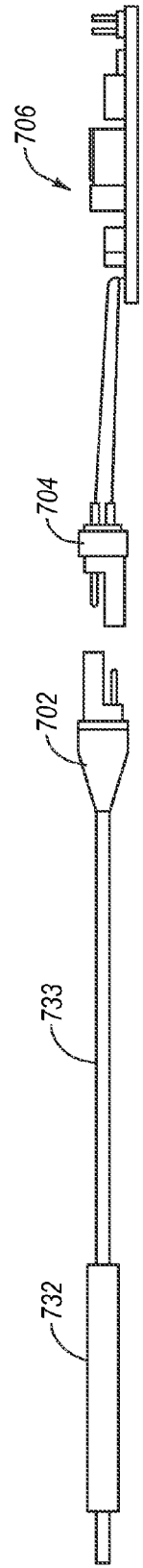
Figure 7C:
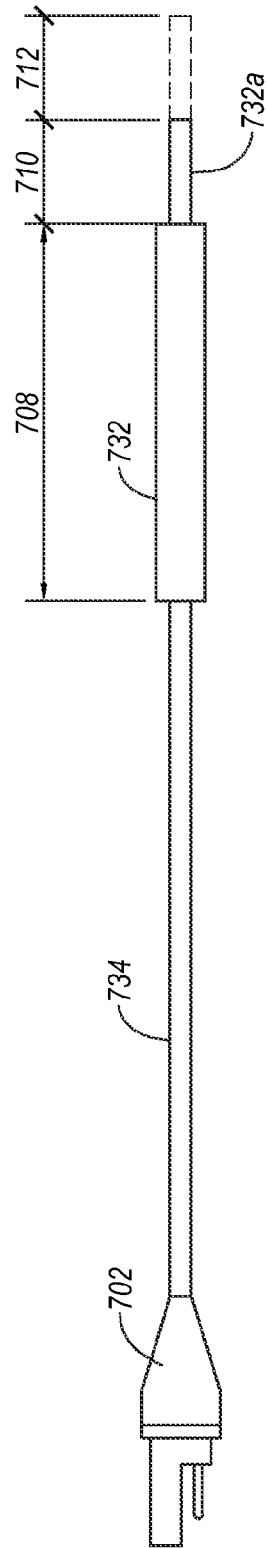
Figure 7D:
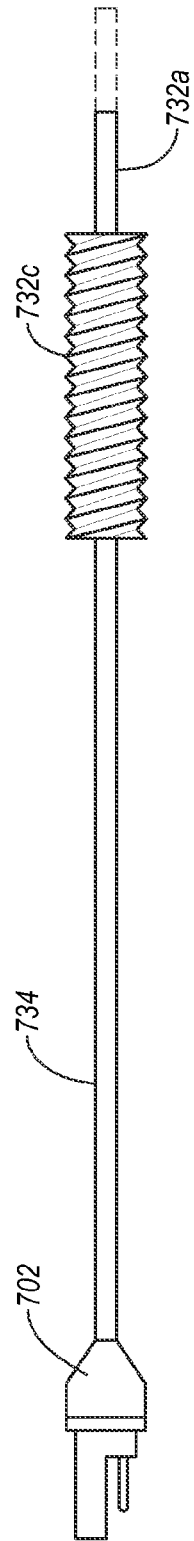

FIGS. 7C-7D show that the DVRT device 732 includes a core 732a. The DVRT device has a length 708, and the core 732a can be modulated so that it has a relative length of from 710 to 712. The change from 710 to 712 allows for the DVRT device 732 to work as a sensor. The DVRT device 732c of FIG. 7D is configured with a threaded body such that it can be screwed into a receiving device. The receiving device (not shown) can be coupled to the cantilever member.

The components of the orofacial stiffness devices shown in the various figures can include components of the other orofacial stiffness devices shown in the other figures.

Figure 2:
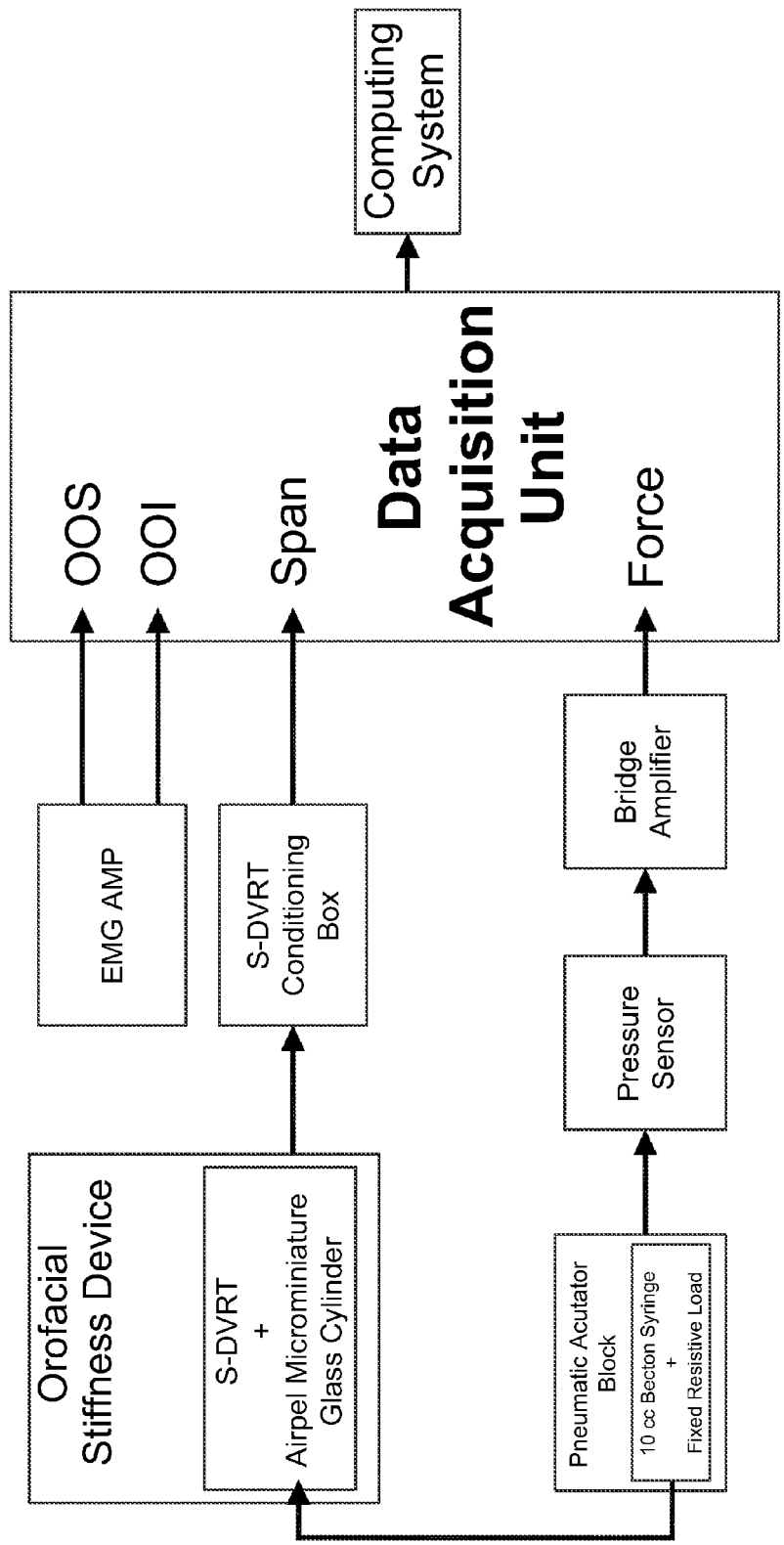
FIG. 2 includes a schematic block diagram of a system for measuring oral/facial stiffness (e.g., orofacial stiffness device and system). The Orofacial stiffness device is equipped with a subminiature differential variable reluctance transducer (DVRT) to measure displacement of the lips, and a pressure transducer to derive the reactive force associated with perioral tissue recoil. A fixed pneumatic resistive load (e.g., 30 gauge blunt tip cannula) permits the moveable cantilevers of the orofacial stiffness device to return to its initial position [$L_0+$15 mm] following each imposed stretch trial.

FIG. 2 shows that the orofacial stiffness device 10 can be part of an orofacial stiffness system 50. The device 10 can be electronically coupled to a signal conditioning box that conditions the signal from the sensor 32 before it is provided to a data acquisition system. The pressure member 38 can be fluidly coupled to a pressure actuator that can change the pressure of the pressure member 38 and/or move the lip hooks 20 with respect to each other. The pressure actuator is operably coupled with a pressure sensor that can sense pressure changes from the lips and/or pressure actuator, which in turn provides data to a bridge amplifier (or other digital data conditioner) before the data is provided to the data acquisition system. Additionally, the data acquisition system is electronically coupled to the OOS electrodes 12 and OOI electrodes 14 through an EMG amplifier. All digital data processed through the data acquisition system can be provided to a computing system for processing, manipulation, and any other functionality applied to data.

In one embodiment, a device for measuring oral/lip stiffness in a subject can include two components configured for being placed at the corners of a patients mouth so as to be capable of applying pressure to the corners of the mouth or receive pressure from the corners of the mouth (e.g., lip hooks). The two lip hook components can be coupled to a cantilever member so that the two lip hook components are capable of being moved closer together or further away from each other. Accordingly, the two lip hook components can be coupled to two separate elongate members that are part of the cantilever member. The two elongate members can be pivotally coupled to a pivot member in order to provide a cantilever member. The pivot member can be opposite of the two lip hook components with respect to the elongate members. Each of the two elongate members can be coupled (directly or indirectly) to an electronic sensor that is configured to sense the stiffness of the lips by sensing movement of the elongate members with respect to the pivot point, where the electronic sensor is operably coupled to each of the elongate members. Also, a pressure component is coupled to the two elongate members (directly or indirectly) such that the pressure component can provide a pressure to the cause the elongate members to move with respect to the pivot point so as to provide pressure to and/or receive pressure from the two lip hooking components.

The device can be provided and/or used with or without electrodes. However, electrodes can be useful for measuring the changes or dynamics of orofacial stiffness. The electrodes can be part of an electrode system, where various electrodes record data for different muscles or muscle areas. The electrode system can include an electrode configured for measuring the orbicularis oris superior (OOS), and an electrode for measuring the orbicularis oris inferior (OOI). The electronic system can be configured for determining whether the patient is actively moving, holding, or tensing their lips as well as relaxation of the lips. Accordingly, the electrode system can include an electrode pair for monitoring the OOS, an electrode pair for monitoring the OOI, and a reference electrode. Also, the electrode system can be coupled/couplable to a computing system.

The orofacial stiffness device can be associated with a bite block. While the bite block is not coupled to the orofacial stiffness device as described herein, the bite block and device could be coupled together. Also, the bite block can be provided separately or in a kit or system with the device. The bite block can be configured as any bite block. For example, the bite block can be configured to prevent the patient from biting down or otherwise moving their lower jaw during an orofacial stiffness test.

One of the advancements of the orofacial stiffness device described herein is the lack of requirement for head restraint of the patient undergoing an orofacial stiffness test. However, it can be beneficial if the orofacial stiffness device can be associated with a reference point on the human anatomy. As such, the orofacial stiffness device can include an integrated or removably couplable anchor for anchoring the device to the patient. The anchor can be configured to anchor to the patient's nose, chin, or other facial feature.

The orofacial stiffness device can be associated with a computing system such that the computing system can be in communication with the electronic sensor, pressure component, and/or the electrodes of the electrode system.

In one embodiment, the two lip hook components can be any two hooking means that are capable of hooking the corners of a patient's mouth. The hooking means can include a hook, protrusion, bar, post, or other configuration of a component that can be received into the corners of a mouth for operation as described herein.

In one embodiment, the two elongate members can form an even arm cantilever with the pivot member in a "X" shape or a "V" shape. However, the shape may be varied as long as there are two elongate members, where the two members can be of the same or different length as well as shape. The sensor can be configured such that the shape of the two elongate members can be modulated while retaining functionality.

In one embodiment, the electronic sensor means can be a sensor is a differential variable reluctance transducer. Such differential variable reluctance transducers are well known in the art.

In one embodiment, the pressure component is a pressure actuator. However, the pressure component can be any pressure means for supplying or receiving pressure with respect to the lip corners.

In one embodiment, the present invention includes a kit or system for measuring oral/lip stiffness in a subject. Such a kit or system can include the orofacial stiffness device as described herein. Additionally, the system or kit can include: a bite block; replacement lip hooks; additional sensors (optionally with different configurations); different pressure components, various nose or chin (or even forehead) anchors; an electrode system; and/or a computing system. The pressure component can be a pressure actuator having first and second ends being operably coupled with two different arms of the cantilever. The electrode system can include an electrode pair for monitoring the orbicularis oris superior (OOS), an electrode pair for monitoring the orbicularis oris inferior (OOI), and a reference electrode. The computing system can be configured to provide and/or receive data from the pressure actuator, differential variable reluctance transducer (e.g., sensor), and electrode system so as to be capable of receiving and/or transmitting data therebetween.

In one embodiment, the anchor can include an adhesive member configured for adhering the anchor to the subject. The adhesive can be any medical grade adhesive such as a pressure sensitive adhesive like silicone adhesive.

In one embodiment, the orofacial stiffness system can include a pressure generating device. The pressure actuator can be removably fluidly coupled to the pressure generating device such that pressure generated thereby can provide the pressure to the pressure actuator. The pressure generating device can be any type of pump that generates pressure.

In one embodiment, the orofacial stiffness system can include the data conditioning device being in communication with a data acquisition system. As such, data from the data conditioning device can be acquired, stored, transmitted, and/or provided to a computing system.

In one embodiment, the electrode system being in communication with an EMG amplifier. Also, the EMG amplifier can be in communication with the data acquisition system. As such, the electrode data can be processed through the EMG amplifier before being provided to the data acquisition system of computing system.

In one embodiment, the pressure actuator can be in communication with a pressure sensor. The pressure sensor can then sense the pressure provided or received by the pressure actuator with respect to the lip hooks, and convert the pressure into pressure data. The pressure data can be useful for the orofacial stiffness test so that the orofacial stiffness can be associated with pressures. Also, the pressure generating device being in communication with the pressure sensor, which allows for the pressure generated to be monitored, recorded, and analyzed with the corresponding data from the sensor. The pressure sensor can be in communication with a bridge amplifier so that the pressure data is conditioned for being received into the data acquisition system.

In one embodiment, the data acquisition system can be in communication with a computing system. Alternatively, the computing system can include a data acquisition system.

In one embodiment, a kit or system having the orofacial stiffness device can also include a caliper measuring device. The caliper measuring device can be useful for measuring features of the face, lip corner distance, and for obtaining baseline parameters prior to performing an orofacial stiffness test.

As described herein, the orofacial stiffness device can be used in methods for measuring orofacial stiffness. Accordingly, one embodiment can include a method of measuring oral/lip stiffness (e.g., orofacial stiffness) in a subject. Such a method can include: attaching OOS and OOI electrodes to the skin associated with the OOS and OOI, respectively; attaching the reference electrode to the skin in a location not associated with the OOS or OOI; measuring the mouth length between the corners of the mouth of the subject with the caliper measuring device; determining the resting size of the oral/lips of the subject; adjusting the lip hooks to correspond with the resting size of the oral/lips; placing bite bock in the subject's mouth; operating the data acquisition system to record oral/lip data; increasing pressure in the pressure actuator to stretch the oral/lips apart; allowing the oral/lips to recoil; and record and/or manipulate data related to stretching and recoiling of the oral/lips with the computing system.

In one embodiment, the stiffness testing method can include instructing the patient to remain speechless and motionless, and relax oral/lips without movement or pressure. This can be important to establish a baseline for the orofacial stiffness to be compared against.

In one embodiment, the pressure actuator can be pressurized so as to stretch the mouth/lips. The pressure actuator can be computer controlled, automatic, or manual (e.g., with a syringe type pump). The pressure actuator can then be depressurized. During the pressurizing and depressurizing, the orofacial stiffness can be tested.

During the test, the cantilever arms can be allowed to return to original resting position. The cycle of pressure and lip corner movement can then be induced.

In one embodiment, the orofacial stiffness test can include measuring an interangle oral aperture at rest. Also, the interangle oral aperture can be measured under stress or pressure from the pressure actuator. The interangle oral aperture can provide useful information regarding the orofacial stiffness of the patent. For example, the interangle oral aperture measure can be useful for estimating resting muscle length of oral/lips.

Previously, measurement of orofacial stiffness was tedious and time consuming. Now, however, the orofacial stiffness can be measured with the device described herein in 2 minutes or less. This substantially improves the experience of the patient because (1) the orofacial stiffness test does not require a head restraint and (2) the test can be performed exceedingly fast for a medical procedure.

In one embodiment, the data obtained from the orofacial stiffness test can be digitalized for use, manipulation, or storage in a computing system. The digitized data can be from the pressure actuator and/or differential variable reluctance transducer as well as the electrodes.

The data obtained from the orofacial stiffness test can be used for calculating stiffness coefficients in real time during elastic recoil of the lips. Accordingly, meaningful information, such as the stiffness coefficients, can be obtained relatively fast, which can include being obtained during the orofacial stiffness test. The stiffness coefficient can then be graphically displayed versus lip or mouth span. Also, this can be useful for determining stiffness for a specific span. A specific span is considered a specific distance from corner to corner of the mouth. As such, there can be different stiffness parameters for different mouth spans.

In one embodiment, the data from the orofacial stiffness test can be useful for determining muscle activity patterns during non-passive stretching of the lips/mouth. As such, during the orofacial stiffness test during the non-passive stretch, the muscle patters from the OOS and/or OOI as well as for any other electrode can be monitored to determine muscle activity. The muscle activity may be useful in correlations with diseases or conditions described herein.

In one embodiment, the orofacial stiffness test can include performing a calibrating procedure so as to calibrate the device/system. Calibration procedures can be useful for improving the reliability of the data obtained from the test.

EXPERIMENTAL

Twenty healthy adults (10 males, 10 females), 19 to 31 years of age with no prior history of neurological and craniofacial disorder, and/or speech impairment participated in the study described herein (Table 1).

The subjects were each seated in a comfortable chair, and instructed to remain speechless and motionless, and relax facial muscles during the 2 minute sampling. To ensure the subjects' nonparticipation during the imposed perioral stretch, Ag/AgCl 4-mm diameter bipolar electrodes (2-cm interelectrode distance) were placed over the orbicularis oris superior (OOSm) and orbicularis oris inferior (OOIm) muscles. Biopotentials were conditioned with Grass P511 bioamplifiers (30 Hz-1kHz bandpass, Gain=20K). A 1-cm interincisal bite block was molded (KERR Xtrude-XP™) for each subject to stabilize the mandible during stiffness sampling.

The thin wall tubular stainless steel face-referenced orofacial stiffness device (mass=40.7 gm) was coupled bilaterally to the oral angles via lip saddles (i.e., mouth corners) and supported on the mental symphysis with a double-adhesive tape collar for vertical stabilization. The orofacial stiffness device incorporates an Airpel® custom microminiature pneumatic glass-cylinder actuator instrumented for pressure (Honeywell #26PCCFAG, +/−15 psi) and an integrated custom subminiature displacement sensor (differential variable reluctance transformer [DVRT], MicroStrain®, Inc) to encode lip aperture. The pneumatic actuator was manually pressurized with a 10-cc syringe which in turn imposed an interangle stretch of approximately 20 mm. A 30-gauge blunt tip cannula, vented to atmosphere, was coupled in parallel with the orofacial stiffness pneumatic system. This cannula provided a fixed resistive load, essentially a controlled air leak, upon which the perioral recoil force would act to allow the equal-arm scissor cantilevers to return to their initial lip aperture resting position ($L_0$+15 mm).

Interangle oral aperture at rest provides an estimate of resting muscle length ($L_0$) and was measured with a digital caliper for each subject. The orofacial stiffness interangle span was initialized to [$L_0$+15 mm] for all subjects. A series of 5 interangle stretch trials were completed while simultaneously sampling force, displacement, and electromyograms (EMG) from bipolar electrodes placed on the upper lip (OOSm) and lower lip (OOIm) in real-time with custom software (orofacial stiffness v.3.0.4) written in LabVIEW™ 8.0. Individual interangle stretch trials were completed within 10 seconds, and the perioral stiffness protocol was completed within 2 minutes for each participant.

Air pressure within the microminiature pneumatic glass-cylinder actuator and the displacement signal from the DVRT were digitized at 2 ksamples/sec at 16-bits resolution (National Instruments PCI-6052E multifunction I/O). These waveforms were down-sampled to yield 100 pressure and position samples which were digitally low-pass filtered ($f_{lp}$=30 Hz, 2-pole Butterworth), and subsequently averaged in 10 bins of 10, yielding an effective sample rate of 200 Hz for real-time calculation and display of force, displacement, and derived stiffness.

Figure 3:
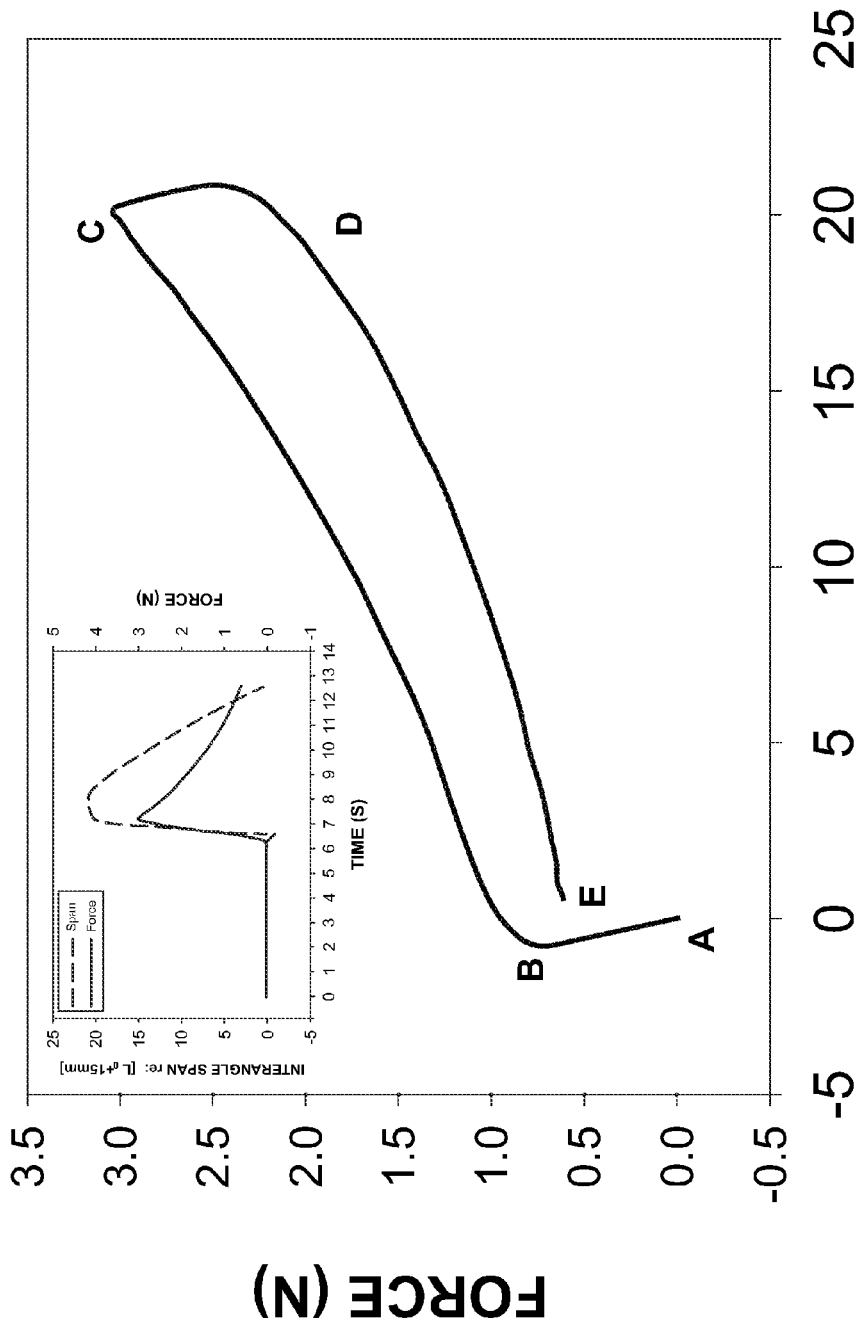
FIG. 3 includes a graph that illustrates a typical force-span hysteresis curve sampled from a normal adult subject with graphic insert showing span-time (black line) and force-time (dashed line) plots. Point A: preload condition of the orofacial stiffness device on a subject's face; B: onset of interangle stretch phase; C: peak interangle stretch; the recoil phase (D-E) during which stiffness is calculated (ΔForce/ΔSpan). Regions from A-E and just after C reflect bending (elasticity) of the orofacial stiffness device without change in S-DVRT position output.

Stiffness coefficients (N/mm) were automatically calculated in real time during the phase of elastic recoil for each of 5 trials as the low-mass interangle yokes of the orofacial stiffness device returned to the participant's interangle rest position. The stiffness coefficient was calculated as the change in force over a 1 mm change in interangle span and sequentially evaluated at 1 mm intervals. Real-time display of stiffness coefficient versus span began when 3 conditions were met simultaneously: span>0.5 mm, force decreasing, and a positive slope for a 10-point linear fit of force versus span. Graphic display continues until span<0.5 mm (see FIG. 3, points D to E). The absolute number of stiffness points along the recoil trajectory depends on the maximum interangle span achieved. To determine stiffness for a specific span a 100-point running cubic spline was evaluated at 0.5 mm above and below the desired span (i.e., force was evaluated at 19.5 and 18.5 mm to calculate stiffness for a nominal span of 19 mm). The cubic spline allows force to be determined at regular displacement intervals.

The root-mean-square (RMS) of the upper lip (OOSm) and lower lip (OOIm) EMG signals were computed during the phase of elastic recoil for each of 5 trials with an increment of 10 samples at 2000 Hz (averaging time of 5 ms) to quantitatively verify non-participation of perioral muscles during sampling.

The DVRT factory calibration data as well as digital caliper measurements were used to determine the ratio of DVRT position-to-interangle span. Force was calibrated with a load cell placed between the stainless steel interangle lip saddles of the orofacial stiffness device. Device stiffness was determined by clamping the stainless steel interangle lip saddles and measuring position and force while modulating pressure with the 10-cc Becton syringe. The device functionality was verified using a precision linear spring.

After orofacial stiffness program initialization (e.g., a computer program configured to perform and/or record data for the orofacial stiffness test), voltage offsets were determined with pressure vented to atmosphere, position set to zero, and EMG disconnected. All four signals were scaled linearly using these offsets and previously determined calibration slopes to yield force (N), displacement (mm), and EMG (uV). The DVRT position signal was converted to interangle span by multiplying by a constant to account for differences in the scissor-equal arm cantilever lengths on opposite sides of the central pivot needle bearing, and by correcting for device stiffness. Measured force is divided by this effective device stiffness and subtracted from position to yield interangle span. The negative slope seen in FIG. 3 between points A and B, and C and D represents the effective device stiffness.

Given the hierarchically nested design of the data, in which the perioral stiffness was measured through a series of 5 interangle stretch trials (level-1) for each participant (level-2), multilevel regression analysis was conducted using SAS Version 9.1 (SAS Institute, 2004). First, an unconditional means model (i.e., null model) was fit in order to determine the random variance components. Then, level-1 and level-2 predictors and cross-level interaction terms were introduced into the null model with their significant random effects. The level-1 predictors represented the linear and quadratic regression slopes of the interangle span on the perioral stiffness. The cross-level interaction terms represented the sex differences in the linear and quadratic regression slopes.

The fitted null model showed that the estimated mean stiffness score across all trials and all participants was 0.073 N/mm (SE=0.002, t [19]=40.90, p<0.01). The fifed null model is: $Y_{ij}=\gamma_{00}+u_{oj}+r_{ij}$, where $u_{oj}\sim N(0,\tau_{00})$ and $r_{ij}\sim N(0,\sigma^2)$ for trial i and participant j. This model expresses the stiffness scores as the sum of an overall mean ($\gamma_{00}$), a series of random deviations from that mean ($u_{oj}$), and a random error ($r_{ij}$) associated with the $i^{th}$ trial in the $j^{th}$ participant. The estimated variances of level-1 and level-2 residual errors were 0.00180 (SE=0.00006, z=30.28.002, p<0.01) and 0.00005 (SE=0.00002, z=2.17, p<0.05), respectively. The intra-class correlation (ICC) indicated that most of the variability (97.6%) in the stiffness scores occurred within participants. These estimates suggested that the stiffness scores do differ within participants and there is less but significant variation between participants.

The final model included two level-1 predictors that represent the linear and quadratic regression slopes of the interangle span on the perioral stiffness. Two cross-level interaction terms were also included to test whether the regression slopes differ between males and females. This model can be written by $$\text{Stiffness}_{ij} = \gamma_{00} + \gamma_{01}\text{Sex}_j + \gamma_{10}\text{Span}_{ij} + \gamma_{20}\text{Span}_{ij}^2 + \gamma_{11}(\text{Sex}_j \times \text{Span}_{ij}) + \gamma_{21}(\text{Sex}_j \times \text{Span}_{ij}^2) + u_{1j}\text{Span}_{ij} + u_{0j} + r_{ij}, \quad (1)$$

$$\text{where} \begin{pmatrix} u_{oj} \\ u_{1j} \end{pmatrix} \sim N\left[\begin{pmatrix} 0 \\ 0 \end{pmatrix}, \begin{pmatrix} \tau_{00} & \tau_{01} \\ \tau_{10} & \tau_{11} \end{pmatrix}\right]$$

and $r_{ij}\sim N(0,\sigma^{-2})$ for trial i and participant j.

The parameter estimates from the fitted final model are shown in Table 2. It was shown that the perioral stiffness increased as a quadratic function of the interangle span, $\hat{\gamma}_{10}$=0.00054, t (1811)=37.28, p<0.01. More importantly, this quadratic slope significantly differed between males and females, $\hat{\gamma}_{21}$=0.00005, t (1811)=2.31, p<0.05. Although the linear function of the interangle span was also significant, there was no sex difference in this linear slope.

The residual ICC showed that 43.1% of total residual variance occurred between participants. The squared multiple correlation indicated that approximately 89.3% of level-1 residual variance ($\hat{\sigma}^2$) was accounted for by this model. Since the estimated level-2 residual variance ($\hat{\tau}_{00}$) increased with the random slope, the squared multiple correlation for this level could not be obtained. The likelihood-ratio (LR) test suggested that both the random intercept (LR $\chi^2$=232.10, p<0.01) and the random linear slope (LR $\chi^2$=1439.00, p<0.01) were tenable.

Perioral muscle activity remained remarkably constant as interangle span was increased confirming the non-participatory nature of the experimental task. The distribution of EMG RMS values for the OOS and OOI muscle recording sites pooled among subjects is shown in FIGS. 5A and 5B. A one-way ANOVA analysis for EMG RMS versus interangle span indicated non-significance for both the upper lip (F=0.80, p=0.737, R-sq (adj)=0.00%), and lower lip (F=0.54, p=0.96°7, R-sq (adj)=0.00%) and confirmed the non-participatory nature of the stiffness sampling protocol.

Figure 4:
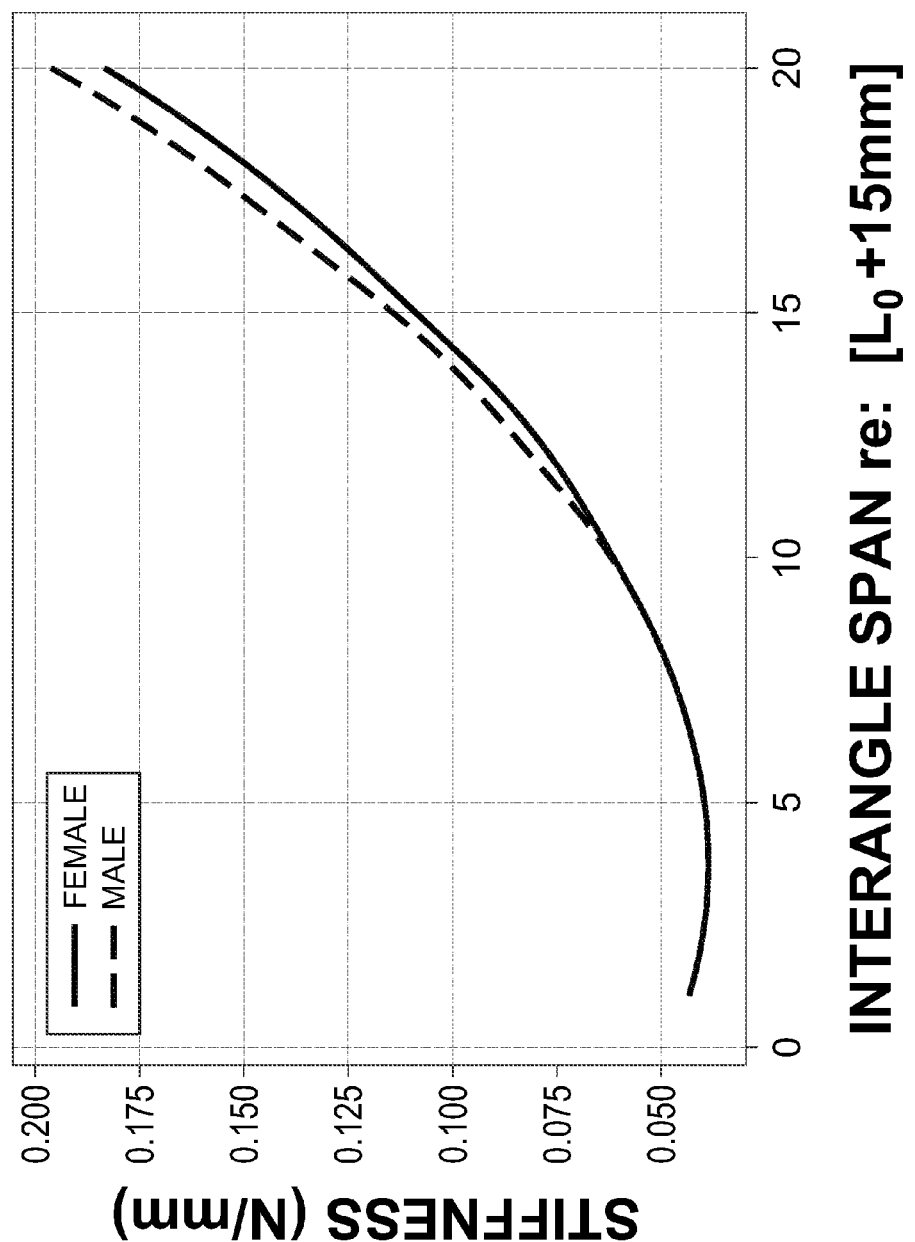
FIG. 4 includes a graph that illustrates regression functions for male (dotted line) and female subjects (solid line).

This above orofacial stiffness protocol is a non-invasive and rapid (<2 mins) method for real-time data acquisition and analysis of perioral tissue stiffness without head restraint. The derived regression function for non-participatory perioral stiffness using the orofacial stiffness device is consistent with previous reports in healthy participants using costly servo-controlled linear actuators that required head restraint. The results indicated that intersubject variability in stiffness growth functions increased as the interangle span increased (FIG. 4). This is likely due to individual differences in perioral anatomy. The fact that male subjects yielded significantly higher stiffness coefficients than female subjects is likely due to the differences in anatomy and mass of contractile/connective tissue elements in the lower face. Increased allometrics, or greater tissue mass among males likely translates to larger muscles and soft tissue attachments. Thus, gender is a significant factor when assessing perioral stiffness.

The clinical utility of the orofacial stiffness device was put to the test in a participant with a significant movement disorder, a 68-year old male with advanced idiopathic Parkinson's disease (PD). This participant had a 12-year history of PD and exhibited moderate-severe dyskinesia of head, trunk, and extremities under the prescribed dosage of anti-PD medications in the ON state. He exhibited reduced dyskinesia, but increased dystonia and rigidity in the OFF condition (unmedicated). This individual consented to refrain from taking his anti-PD medications from the previous evening for a period of 12-hours, and subsequently arrived at the laboratory at 9 AM in the OFF condition. An incisal bite block was molded, and the orofacial stiffness protocol was completed in less than 2 minutes. The participant was given his prescribed dose of anti-PD medications with a glass of water. After 50 minutes, the participant was in the ON state, and the orofacial stiffness protocol was repeated once again to assess the effects of L-Dopa on perioral stiffness functions.

Several striking features are apparent from the PD stiffness plots given in FIG. 6. First, in the OFF state (unmedicated), perioral stiffness is approximately 7 times greater than normal, and because of this high level of tonic muscle activity, the imposed displacements generated by the orofacial stiffness device were limited to approximately 10 mm beyond resting span ($L_0+15$ mm). Administration of the anti-PD medications had a significant effect on reducing the slope and offset of the quadratic stiffness function, however perioral stiffness remained significantly elevated over normal levels.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein by specific reference.

Tables

TABLE 1

Physical characteristics of participants.

|  | Male | Female |
|---|---|---|
| Number of Subjects | 10 | 10 |
| Age (yrs) | 24.59 (SD = 3.07) | 23.18 (SD = 2.76) |
| Weight (kg)* | 67.78 (SD = 7.35) | 57.52 (SD = 8.44) |

TABLE 1-continued

Physical characteristics of participants.

|  | Male | Female |
|---|---|---|
| Height (cm)* | 174.22 (SD = 11.12) | 164.74 (SD = 4.22) |
| Head circumference (cm) | 57.05 (SD = 1.66) | 55.69 (SD = 2.07) |
| Nasion-to-inion (cm) | 39.22 (SD = 2.23) | 37.54 (SD = 1.75) |
| Lip Resting Span (mm) | 47.32 (SD = 2.82) | 46.46 (SD = 2.16) |

*Significant difference at $p < .05$

TABLE 2

Multilevel regression parameter estimates of between- and within-level components.

| Fixed Effect | Estimate | SE | t | p |
|---|---|---|---|---|
| Intercept | .04583 | .00408 | 11.23 | <.01 |
| Sex | .00099 | .00579 | .17 | .86 |
| Span | −.00396 | .00107 | −3.70 | <.01 |
| Span$^2$ | .00054 | .00002 | 37.28 | <.01 |
| Sex × Span | −.00046 | .00152 | −.30 | .76 |
| Sex × Span$^2$ | .00005 | .00002 | 2.31 | <.05 |

| Random Effect | Estimate | SE | z | p |
|---|---|---|---|---|
| $\sigma^2$ | .00019 | .00000 | 30.09 | <.01 |
| $\tau_{00}$ | .00015 | .00005 | 2.82 | <.01 |
| $\tau_{11}$ | .00001 | .00000 | 2.97 | <.01 |
| $\tau_{01}$ | −.00004 | .00001 | −2.81 | <.01 |
| ICC | .431 | | | |
| $R^2_{trial}$ | .893 | | | |
| $R_{participant}$ | — | | | |
| −2lnL | −10360.1 | | | |
| AIC | −10352.1 | | | |

The invention claimed is:

1. A device for measuring orofacial stiffness in a subject having lips, the device comprising:
   two lip saddle attachment components configured for attachment to the lip saddles of the subject's mouth;
   two elongate members comprised of a first elongate member and a second elongate member, each being coupled with one of the lip saddle attachment components;
   a pivot member that couples the two elongate members at a pivot point at a distance from the two lip saddle attachment components;
   an electronic sensor mounted between the two elongate members and configured to sense stiffness of the subject's lips by sensing movement of the elongate members with respect to the pivot point, where the electronic sensor is coupled to each of the elongate members; and
   a pressure component mounted between the two elongate members and configured to move with respect to the pivot point so as to provide pressure-actuated displacement to increase a horizontal lip aperture of the subject's lips and/or receive pressure from the lip saddle attachment components,
   wherein one of the electronic sensor or pressure component is directly coupled to two movable coupling members comprised of a first movable coupling member and a second movable coupling member and the other of the electronic sensor or pressure component is indirectly coupled to the two movable coupling members, wherein the first movable coupling member is coupled to the first elongate member and the second movable coupling member is coupled to the second elongate member, and the first movable coupling member and second movable coupling member being coupled to opposite ends of the one of the electronic sensor or pressure component.

2. A device as in claim 1, further comprising:
an electrode system for measuring changes in an orbicularis oris superior (OOS) and orbicularis oris inferior (OOI) of the subject, which electrode system being configured for determining whether the subject is actively moving, holding or tensing the lips.

3. A device as in claim 2, the electrode system further comprising an electrode pair for monitoring the OOS, an electrode pair for monitoring the OOI, and a reference electrode.

4. A device as in claim 3, further comprising a bite block.

5. A device as in claim 4, further comprising an anchor configured for anchoring the device to the subject.

6. A device as in claim 5, wherein the anchor is configured as a chin anchor or nose anchor.

7. A device as in claim 6, further comprising a computer system capable of being in communication with the sensor and the pressure component, and with the electrode system.

8. A device as in claim 7, characterized by at least one of the following:
the two lip saddle attachment components each include a feature configured for attachment to the lip saddles of the subject's mouth;
the two elongate members form an even arm cantilever in a "X" shape or a "V" shape;
the pivot point forms an intersection of the two elongate members;
the electronic sensor is a differential variable reluctance transducer; and
the pressure component is a pressure actuator.

9. A device as in claim 8, wherein one or more of the two lip saddle attachments components has an adjustment mechanism configured for widening or shortening distance between the features configured for attachment to the two lip saddles.

10. A device as in claim 9, wherein the electronic sensor and the pressure component each have elongate bodies so as to extend the elongate bodies between the elongate members so that opposite ends of the elongate bodies are coupled to the elongate members through the movable coupling members.

11. A device as in claim 1, wherein the pressure component is a pressure actuator.

12. A device as in claim 11, further comprising a pressure generating component operably coupled to the pressure component.

13. A device as in claim 12, wherein the sensor is mounted on the pressure component and the pressure component is directly coupled to the elongate members through the two movable coupling members.

14. A device as in claim 12, wherein the sensor is coupled to both of the elongate members through the movable coupling members.

15. A system for measuring orofacial stiffness in a subject, the system comprising:
a device of claim 1;
a bite block;
an anchor coupled with the device, said anchor configured for anchoring the device to the subject;
an electrode system having an electrode pair for monitoring changes in an orbicularis oris superior (OOS) of the subject, an electrode pair for monitoring changes in an orbicularis oris inferior (OOI) of the subject, and a reference electrode; and
a computer system in communication with the pressure component, the electronic sensor, and the electrode system so as to be capable of receiving and/or transmitting data therebetween.

16. A system as in claim 15, further comprising an adhesive member configured for adhering the anchor to the subject.

17. A system as in claim 16, wherein the anchor is a chin anchor or a nose anchor.

18. A system as in claim 17, characterized by one or more of the following:
the pressure component being a pressure actuator that is fluidly coupled to a pressure generating device;
the sensor being mounted on the pressure component;
the sensor being in communication with a data conditioning device;
the data conditioning device being in communication with the computer system;
the electrode system being in communication with an EMG amplifier;
the EMG amplifier being in communication with the computer system;
the pressure actuator being in communication with a pressure sensor;
the pressure generating device being in communication with the pressure sensor and;
the pressure sensor being in communication with a bridge amplifier.

19. A system as in claim 18, further comprising a caliper measuring device.

20. A method of measuring orofacial stiffness in a subject, the method comprising:
providing the system in claim 15;
attaching the OOS and OOI electrodes to skin associated with the OOS and OOI, respectively;
attaching the reference electrode to the skin in a location not associated with the OOS or OOI;
measuring a mouth length between the lip saddles of the subject with a caliper measuring device;
determining a resting distance between the lip saddles of the subject;
adjusting the lip saddle attachment components to correspond with the resting distance between the lip saddles;
attaching the lip saddle attachment components to the lip saddles of the subject;
placing the bite bock in the subject's mouth;
operating the computer system to record data;
increasing pressure in the pressure component to stretch the lip saddles apart;
allowing the lip saddles to recoil; and
recording and/or manipulating data related to stretching and recoiling of the lip saddles with the computer system.

21. A method as in claim 20, further comprising one or more of the following:
instructing the subject to remain speechless and motionless, and relax the lips without movement or pressure;
manually pressurizing the pressure component so as to stretch the lip saddles;
allowing the two elongate members of the device to return to an original resting position;
measuring an interangle oral aperture at rest;
estimating a resting muscle length of the lips;
completing measurement of lip stiffness in 2 minutes or less;
digitizing data from the pressure component and the electronic sensor;

calculating stiffness coefficients in real time during elastic recoil of the lip saddles;
graphically displaying a stiffness coefficient versus a lip saddle span;
determining a stiffness for a specific lip saddle span;
determining a muscle activity pattern during a non-passive stretch; or
calibrating the system.

\* \* \* \* \*